(12) United States Patent
Poston et al.

(10) Patent No.: US 7,638,287 B2
(45) Date of Patent: Dec. 29, 2009

(54) DETECTING AND PREDICTING PRE-ECLAMPSIA

(75) Inventors: Lucilla Poston, London (GB); Andrew Shennan, London (GB)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

(21) Appl. No.: 11/623,480

(22) Filed: Jan. 16, 2007

(65) Prior Publication Data

US 2007/0178530 A1   Aug. 2, 2007

(30) Foreign Application Priority Data

Jan. 17, 2006   (GB)   ................. 0600916.1

(51) Int. Cl.
*G01N 33/68* (2006.01)
*G01N 33/53* (2006.01)

(52) U.S. Cl. ................ 435/7.1; 702/19; 435/4
(58) Field of Classification Search ........... None
See application file for complete search history.

(56) References Cited

FOREIGN PATENT DOCUMENTS

| WO | WO 98/28006 | 7/1998 |
|----|-------------|--------|
| WO | WO 02/37120 A2 | 5/2002 |
| WO | WO 02/37120 A3 | 5/2002 |

OTHER PUBLICATIONS

Williams et al Am J Epidemiol 1999;149:323-329.*
Bower et al. Obstetrics and Gynecology, 1993,82,78-83.*
Merviel et al. European Journal of Obstetrics & Gynecology and Reproductive Biology , vol. 115, Issue 2, 2004, pp. 134-147.*
Reith A et al: "Plasminogen activator inhibitors (PAI-1 and PAI-2) in normal pregnancies, pre-eclampsia and hydatidiform mole." British Journal of Obstetrics and Gynaecology, vol. 100, No. 4, 1993, pp. 370-374, XP008005703, ISSN: 0306-5456.

Estelles A et al: "Changes In The Plasma Levels Of Type 1 And Type 2 Plasminogen Activator Inhibitors In Normal Pregnancy And In Patients With Severe Preeclampsia" Blood, vol. 74, No. 4, 1989, pp. 1332-1338, XP008005702. ISSN: 0006-4971.
Torry D S et al: "Preeclampsia is associated with reduced serum levels of placenta growth factor." American Journal of Obstetrics and Gynecology. Dec. 1998, vol. 179, No. 6 Pt 1, pp. 1539-1544, XP008005712, ISSN: 0002-9378.
Anim-Nyame N et al: "Longitudinal analysis of maternal plasma leptin concentrations during normal pregnancy and pre-eclampsia." Human Reproduction Sep. 2000, vol. 15, No. 9, pp. 2033-2036, XP008005712, ISSN: 0268-1161.
Teppa R J et al: "Free leptin is increased in normal pregnancy and further increased in preeclampsia."Metabolism: Clinical and Experimental. Aug. 2000, vol. 49, No. 8, pp. 1043-1048, XP008005711, ISSN: 0026-0495.
Coleman et al., Drug Discovery Today.2003. 8:233-235.
M. Kolben et al., "Measuring the Concentration of Various Plasma and Placenta Extract Proteolytic and Vascular Factors in Pregnant Patients with HELLP Syndrome, Pre-/Eclampsia and Highly Pathologic Doppler Flow Values," Gynakologisch-Geburtshilflische Rundschau, 1995, vol. 35, Suppl 1, pp. 126-131.
I. S. Serin et al., "Predictive Value of Tumor Necrosis Factor Alpha (TNF-Alpha) in Preeclampsia," European Journal of Obstetrics, Gynecology, and Reproductive Biology, Jan. 10, 2002, vol. 100, No. 2, pp. 143-145.
A.. H. Shennan et al., "Pre-Eclampsia" Contemporary Clinical Gynecology and Obstetrics, 2001, vol. 1, No. 4, pp. 353-364.
L. C. Chappell, et al., "A Longitudinal Study of Biochemical Variables in Women at Risk of Preeclampsia," American Journal of Obstetrics & Gynecology, Jul. 2002, vol. 187, No. 1, pp. 127-136.
International Search Report and Written Opinion.

* cited by examiner

*Primary Examiner*—Michael Borin
(74) *Attorney, Agent, or Firm*—Banner & Witcoff, Ltd.

(57) ABSTRACT

The technology described herein relates to methods of detecting or predicting pre-eclampsia (PE). The technology described herein also relates to commercial packages, such as diagnostic kits, for performing a method of detecting or predicting PE. In particular, the technology described herein provides methods of predicting pre-eclampsia when determining the levels of biochemical markers.

10 Claims, No Drawings

DETECTING AND PREDICTING PRE-ECLAMPSIA

The technology described herein relates to methods of detecting or predicting pre-eclampsia (PE). The technology described herein also relates to commercial packages, such as diagnostic kits, for performing a method of detecting or predicting PE.

PE affects approximately 4% of all pregnancies and is a leading cause of maternal death in the UK, the United States and other nations. This disease, or the threat of onset, is the commonest cause of elective premature delivery, accounting for approximately 15% of all premature births. It is recommended by the UK National Institute for Clinical Excellence (NICE) that women should be assessed for risk of pre-eclampsia (PE) in early pregnancy, to allow a schedule of antenatal care to be tailored. Key principles of management are to identify women with pre-eclampsia, so that appropriate surveillance, (usually as an inpatient), and intervention (usually delivery) can be instigated. Similar guidelines exist in nations throughout the world.

PE is defined according to the guidelines of the International Society for the Study of Hypertension in Pregnancy (Davey et al., Am. J. Obstet Gynecol; 158: 892-98, 1988) as gestational hypertension with proteinuria (for previously normotensive women) or severe PE as severe gestational hypertension with proteinuria (for women with chronic hypertension). For women with chronic hypertension, superimposed PE is defined by the new development of proteinuria. Gestational hypertension is defined as two recordings of diastolic blood pressure of 90 mm Hg or higher at least 4 h apart, and severe pressure of 110 mm Hg or higher at least 4 h apart or one recording of diastolic blood pressure of at least 120 mm Hg. Proteinuria is defined as excretion of 300 mg or more protein in 24 h or two readings of 2+ or higher on dipstick analysis of midstream or catheter urine specimens if no 24 h collection was available. Women are classified as previously normotensive or with chronic hypertension before 20 weeks' gestation. Thus, detection of PE is predominantly carried out using measurement of blood pressure and testing for proteinuria in pregnant women. These procedures and the care of affected women and of the premature children make considerable demands on healthcare resources. Accurate identification of women at risk could dramatically reduce costs of antenatal care.

Although there is no widely used treatment for PE (other than premature delivery), a significant reduction in PE in high risk women given supplements of vitamin C and vitamin E from 16 weeks gestation onwards has been described (see Chappell et al., The Lancet, 354, 810-816, 1999; and Rumbold & Crowther, Vitamin C supplementation in pregnancy (Cochrane Review, 2002, updated 2004). Meta-analysis also suggests that low dose aspirin is effective in reducing the incidence of PE by 15% (Duley et al., Cochrane Review, 2004). A number of other trials of supplements of vitamin C and vitamin E are under way internationally. It is therefore quite possible that a cheap, safe and widely available intervention will shortly be demonstrated to be effective.

More accurate and robust identification of women at risk would target those women most likely to benefit from these prophylactic therapies. Those identified at lower risk could be provided with less intensive and less expensive antenatal care. In addition accurate prediction of those women at risk of PE would enable streaming of healthcare resources to those most at risk, and result in a large saving in health care costs through reduction of antenatal visits for those at low risk.

There is no widely accepted method for the early detection or prediction of PE. Elevation of the blood pressure and detection of protein in the urine occur when the disease process is well established, as indicated above. Detection of an abnormality of the blood flow to the uterine artery by Doppler ultrasound in women who later develop PE has been of some predictive use but this abnormality has been found to be relatively non-specific and for this reason has not been adopted in routine clinical practice.

Although some plasma/urine biochemical markers have been shown to be abnormal in the disease process, no single marker has proven to be of adequate sensitivity for use as a predictive indicator. For example the use of placenta growth factor (PLGF) alone as a predictive indicator of PE has been proposed, but the predictive power of this marker could not be determined with any certainty. For example, International patent application WO 98/28006 suggests detecting PLGF alone or in combination with vascular endothelial growth factor (VEGF) in order to predict the development of PE.

Furthermore, the effect of vitamin supplementation on the maternal blood PAI-1/PAI-2 ratio has previously been published (Chappell et al, 1999, Lancet, 354, 810-816) and others have documented raised PAI-1/PAI-2 in established PE (Reith et al., 1993, British Journal of Obstetrics and Gynaecology, 100, 370-4) and elevated PAI-1 in women who subsequently developed PE (Halligan et al., 1994, British Journal of Obstetrics and Gynaecology, 101, 488-92). PLGF has been shown to be reduced in women with established PE (Torry et al., 1998, American Journal of Obstetrics and Gynaecology, 179, 1539-44) and is suggested to be low prior to the onset of the disease. Leptin has been found to increase with gestation in normal pregnant women (Highman et al., 1998, American Journal of Obstetrics and Gynaecology, 178, 1010-5). Leptin has also been shown to rise even further in established PE, the first report being published by Mise et al., Journal of Endocrinology and Metabolism, 83, 3225-9, 1998. Furthermore, Anim-Nyame et al., Hum. Reprod., 15, 2033-6, 2000, indicates that the elevation of leptin concentrations before PE is clinically evident. This finding is supported by Chappell et al., (American Journal of Obstetrics and Gynecology 2002; 187 (1): 127-36), where it is also indicated that vitamin supplementation reduces plasma leptin in women at risk of PE.

In International patent application WO 02/37120 and Chappell et al., (American Journal of Obstetrics and Gynecology 2002; 187(1): 127-36) a predictive test for PE of good sensitivity and specificity is disclosed. The test is based on specific blood markers alone, namely PLGF in combination with at least one of PAI-2, the ratio of PAI-1 to PAI-2 and leptin. For example, results giving 80% sensitivity for 88% specificity at 24 weeks gestation using the algorithm $\log_e$ (PLGF)-3*(PAI-1/PAI-2) were obtained.

It has now been found that certain combinations of biochemical markers with or without haemodynamic markers provides an improved method for the prediction of PE. In particular, combinations including two or more of the specified biochemical markers, and optionally one or more biochemical marker and/or one or more haemodynamic markers, are effective as early detectors or predictors of PE.

The technology described herein provides methods of predicting pre-eclampsia by determining the levels of biochemical markers. In one aspect, a method of predicting pre-eclampsia (PE) involves determining in a maternal sample obtained from a subject the level of soluble tissue necrosis factor alpha receptor 1 (sTNFαR1) and Matrix Metalloproteinase-9 (MMP-9). In another aspect, a method of predicting PE involves determining in a maternal sample obtained from a subject the level of sTNFαR1 and placental growth factor (PlGF).

It has been found that by making the determinations set out above, it is possible to determine with high specificity and sensitivity whether an individual is likely to develop PE. Specificity is defined as the proportion of true negatives (women who will not develop PE) identified as negatives in the method. Sensitivity is defined as the proportion of true positives (women who will develop PE) identified as positives in the method.

The presence of diastolic notch in the uterine artery waveform is predictive for PE. High values of systolic and diastolic blood pressure (SBP and DBP) and the mean arterial pressure (MAP) are also indicative of subsequent PE. Thus, a method for predicting PE using one or more biochemical markers can additionally include measuring one or more haemodynamic variables. The haemodynamic variable can be any parameter or abnormality associated with PE. For example, the haemodynamic variable can be any parameter or abnormality of a uterine artery waveform obtained from the subject, such as diastolic notch or an abnormal resistance index (for example, an abnormal resistance index (R1) or pulsatility index (P1)). The haemodynamic variable can be blood pressure, such as systolic blood pressure (SBP), diastolic blood pressure (DBP), or mean arterial pressure (MAP, defined as DBP+(SBP−DBP)/3). For example, the systolic blood pressure (SBP), diastolic blood pressure (DBP), or mean arterial pressure (MAP, defined as DBP+(SBP−DBP)/3) of the subject can be determined. The blood pressure of the subject can be determined using any known technique allowing accurate determination of the subject's blood pressure. By additionally determining the blood pressure of the subject, the specificity and sensitivity of the method is further improved. The blood pressure of the subject can be determined from reviewing or analysing blood pressure data obtained from the subject.

A method for predicting PE as described herein can additionally include determining the presence of diastolic notch in a uterine artery waveform obtained from the subject. By additionally determining the presence of diastolic notch, the specificity and sensitivity of the method can be further improved. The uterine artery waveform can be obtained by any suitable method, for example, by Doppler Ultrasound.

It has been found that the specific combinations referred to above are particularly useful for determining whether a subject is likely to develop PE. It also has been found that by measuring markers mentioned above and optionally determining the measurements from the uterine artery waveform and/or blood pressure, that it is possible to determine with high specificity and sensitivity whether an individual is likely to develop PE.

It has been found that in subjects who subsequently developed PE the level of sTNFαR1 was raised. The level of MMP-9 was found to be reduced in such women. Placenta growth factor (PLGF) failed to show the pronounced rise normally observed in healthy pregnancies. PAI-2 was also found to be reduced in such women. The levels of leptin, PAI-1 and ICAM were found to be raised in such women.

Combinations of the markers proved to be highly sensitive and specific for prediction of PE. In particular, combinations including MMP-9 and sTNFαR$_1$, either on their own or with other biomarkers, or with haemodynamic measurements (for example, diastolic notch or blood pressure), have been found to be highly sensitive and specific for prediction of subsequent PE. In such combinations, a positive prediction is given by high sTNFαR$_1$ and low MMP-9, optionally with one or more of low PLGF, low PAI-2, raised SBP, raised DBP, raised MAP and presence of diastolic notch.

In testing the combinations described above it has been found that for subjects who will develop PE (i.e., the prediction is positive) there is no increase in the level of PLGF with gestation, whereas PLGF normally increases with gestation; and the level of MMP-9 is reduced.

Thus, the methods for predicting PE described herein can additionally include determining in a maternal sample obtained from a subject the level of one or more additional markers, for example, one or more of total PLGF, leptin, plasminogen activator inhibitor-1 (PAI-1), sTNFαR1, MMP-9 and intercellular adhesion molecule-1 (ICAM). It has been found that one or more of these additional markers are useful for improving the specificity and sensitivity of the method. As an example, a method in which levels of sTNFαR1 and MMP-9 are determined can additionally include determining the level of plasminogen activator inhibitor-2 (PAI-2) in the maternal sample. By additionally determining the presence of PAI-2, the specificity and sensitivity of the method can be further improved. Additional specific examples of marker combinations are described herein below.

The technology described herein provides a method for predicting PE that includes determining in a maternal sample obtained from a subject the level of soluble tissue necrosis factor alpha receptor 1 (sTNFαR1) and Matrix Metalloproteinase-9 (MMP-9), and determining the presence of a diastolic notch in a uterine artery waveform obtained from the subject, wherein a positive prediction is given by high sTNFαR1, low MMP-9 and the presence of a diastolic notch.

Another method provided by the technology includes determining in a maternal sample obtained from a subject the level of soluble tissue necrosis factor alpha receptor 1 (sTNFαR1), and placenta growth factor (PLGF), wherein a positive prediction is given by high sTNFαR$_1$, and low PLGF. If desired, the method can further include determining the presence of a diastolic notch in a uterine artery waveform obtained from the subject, wherein a positive prediction is given by high sTNFαR$_1$, and low PLGF and the presence of a diastolic notch.

The technology provides a method for predicting PE that includes determining in a maternal sample obtained from a subject the level of soluble tissue necrosis factor alpha receptor 1 (sTNFαR1), Matrix Metalloproteinase-9 (MMP-9) and PLGF, wherein a positive prediction is given by high sTNFαR$_1$, low MMP-9 and low PLGF.

Also provided is a method for predicting PE that includes determining in a maternal sample obtained from a subject the level of soluble tissue necrosis factor alpha receptor 1 (sTNFαR1), Matrix Metalloproteinase-9 (MMP-9) and plasminogen activation inhibitor-2 (PAI-2), wherein a positive prediction is given by high sTNFαR$_1$, low MMP-9 and low PAI-2.

Further provided is a method for predicting PE that includes determining in a maternal sample obtained from a subject the level of soluble tissue necrosis factor alpha receptor 1 (sTNFαR1) and Matrix Metalloproteinase-9 (MMP-9), and determining the subject's systolic blood pressure (SBP), wherein a positive prediction is given by high sTNFαR$_1$, low MMP-9 and high SBP. Alternatively to determining SBP, or in addition, the method can involve determining the subject's mean arterial pressure (MAP), wherein a positive prediction is given by high sTNFαR$_1$, low MMP-9 and high MAP.

The technology described herein provides a method for predicting PE that includes determining in a maternal sample obtained from a subject the level of soluble tissue necrosis factor alpha receptor 1 (sTNFαR1), Matrix Metalloproteinase-9 (MMP-9) and another marker. For example, the other marker can be leptin, wherein a positive prediction is given by high sTNFαR$_1$, low MMP-9 and high leptin. As another example, the marker can be total PLGF, wherein a positive prediction is given by high sTNFαR$_1$, low MMP-9 and low total PLGF. As a further example, the marker can be plasminogen activation inhibitor-1 (PAI-1), wherein a positive prediction is given by high sTNFαR$_1$, low MMP-9 and high PAI-1. As another example, the marker can be ICAM, wherein a positive prediction is given by high sTNFαR$_1$, low MMP-9 and high ICAM.

As used herein, the term "predicting" when used in reference to pre-eclampsia means determining a likelihood, risk or assessment of a possibility for development of pre-eclampsia in an individual during pregnancy. The term includes detecting early PE.

A maternal sample taken from a pregnant woman can be any sample from which it is possible to measure the markers mentioned above. For example, the sample can be blood. Other exemplary types of samples include serum, plasma, other blood fractions, and urine. Levels of biomarkers also can be determined in maternal cells, for example, cells collected from a bodily fluid or a tissue sample such a cytrophoblast and syncytiotrophoblast cells. Maternal samples can be taken at any time from about 10 weeks gestation. For example, the sample can be taken at between 12 and 38 weeks gestation or between 20 and 36 weeks. Furthermore, the maternal sample may be taken during one or more of the following times: 11-14 weeks gestation; 15-17 weeks gestation; 19-21 weeks gestation; and 23-35 weeks gestation.

Soluble tissue necrosis factor alpha receptor 1 (sTNFRα1) is a standard term well known to those skilled in the art. In particular, the sequence of the human form of sTNFRα1 is given in the NCBI Protein database under accession no. GI: 339750, version AAA61201.1. See also Fuchs et al., Genomics, 13, 219-224, 1992. There are numerous ways of detecting sTNFRα1, including the commercially available ELISA assay from R&D Systems.

Matrix Metalloproteinase-9 (MMP-9) is a standard term well known to those skilled in the art. In particular, the sequence of the human form of MMP-9 is given in the NCBI Protein database under accession no. GI: 74272287, version NP_004985.2. There are numerous ways of detecting MMP-9 including the commercially available Oncogene Research Products™ MMP-9 ELISA.

Placenta growth factor (PLGF) is a standard term used in the art and refers to the free form found in the individual unless indicated otherwise. The amino acid sequence of human PLGF is known (see NCBI Protein database, accession no. XP 040405, +. GI: 20149543, version NP_002623.2). There are numerous methods of detecting PLGF including the commercially available Quantikine Human PLGF immunoassay from R&D Systems Inc.

Free PLGF refers to PLGF that is not in a complex with any other protein. The bound form of PLGF refers to PLGF that is a complex with one or more proteins, e.g., Flt1. Plasminogen activator inhibitor-2 (PAI-2) is a standard term used in the art and is clear to those skilled in the art. In particular, the sequence of the human form of PAI-2 is given in the NCBI Protein database under accession no. GI: 1567409, version CAA02099.1. There are numerous methods of detecting PAI-2 including the commercially available Tint Elize PAI-2 kit from Biopool International.

Plasminogen activator inhibitor-1 (PAI-1) is a standard term used in the art and is clear to those skilled in the art. In particular, the sequence of the human form of PAI-1 is given in the NCBI Protein database under accession no. GI: 189542, version AAA60003.1. See also Ginsburg et al., J. Clin. Invest., 78, 1673-1680, 1986. There are numerous methods of detecting PAI-1 including the commercially available Tint Elize PAI-1 kit from Biopool International.

Leptin is a standard term used in the art and is clear to those skilled in the art. In particular, the sequence of the human form of leptin is given in the NCBI Protein database under accession no. GI: 66474463, version AAY46797.1. There are numerous methods of detecting leptin including Auto Delfia assays.

Intercellular adhesion molecule 1 (ICAM) is a standard term used in the art and is clear to those skilled in the art. In particular, the sequence of the human form of ICAM in two isoforms is given in the NCBI Protein database under accession no. GI: 33340673, version AAQ14901.1 and accession no. GI: 33340675, version AAQ14902.1. There are numerous methods of detecting ICAM including Auto Delfia assays.

For the avoidance of doubt the specific sequences of the markers mentioned above are defined with respect to the version present in the database at the priority date of the present application.

The specific sequences of the markers are exemplary. Those skilled in the art will appreciate that polymorphic variants exist in the human population. Such polymorphic variants generally only differ by a few amino acids (e.g., 1 to 5 or 1 to 3 amino acids). Diastolic notch is a standard term well known to those skilled in the art. In particular, the term refers to the dip in the early diastolic phase of the uterine artery wave form which has been associated with later abnormal outcome of pregnancy including preeclampsia (Chien et al., BJOG., 2000, 107(2), 196-208). Diastolic notch can be persistent in the uterine artery Doppler waveform of pregnant women at risk of several different abnormal pregnancy outcomes. The presence of the diastolic notch alone is not indicative of PE.

As indicated above, the uterine artery waveform can be measured using Doppler ultrasound. The use of Doppler ultrasound to measure the uterine artery waveform is well known to those skilled in the art (Chien et al. BJOG. 2000; 107 (2): 196-208).

The uterine artery waveform can be measured at any time from about 10 weeks gestation. For example, the measurement can be taken from 12 weeks gestation or between 20 and 25 weeks.

Methods for performing immunoassays are well known to those skilled in the art, and many commercial systems are available for performing and detecting results of immunoassays. As an example, the AUTODELFIA® and DELFIA® systems (PerkinElmer) are automated systems specifically designed and optimised for performing immunoassays. As will be appreciated, the markers can be detected using any suitable method.

The blood pressure of the subject, such as systolic blood pressure (SBP), diastolic blood pressure (DBP), or mean arterial pressure (MAP, defined as DBP+(SBP−DBP)/3), can be determined using the Microlife BP 3BTO-A oscillometric blood pressure monitoring device, which is available from Microlife, UK. This has been validated for use in Normotensive Pregnancy, Non-proteinuric HBP and Pre-Eclampsia according to a modified British Hypertension Society protocol (Cuckson et al., Blood Pressure Monitoring, 2002, 7(6), 319-324).

In order to determine whether the level of the markers referred to above is greater than (high) or less than (low) normal, the normal level of the relevant population of pregnant women is typically determined. The relevant population can be defined based on, for example, ethnic background or any other characteristic that can affect normal levels of the markers. The relevant population for establishing the normal level of the markers is, for example, selected on the basis of low risk for PE (i.e., no known risk marker for PE, such as previous PE, diabetes, prior hypertension etc.). Once the normal levels are known, the measured levels can be compared and the significance of the difference determined using standard statistical methods. If there is a substantial difference between the measured level and the normal level (i.e., a statistically significant difference), then there is a clinically important risk that the individual from whom the levels have been measured will develop PE. This risk can be quantified and expressed as a percentage by the use of likelihood ratios.

For example, a risk determination can include determining the standard deviation score for each marker and measurement (except the presence or absence of a diastolic notch), based on the distribution of the values observed in healthy pregnant women of the same gestation who do not go on to develop PE. The determination can additionally include combining the standard deviation scores into a single combined predictor, based either on logistic regression or on multivariate modelling of the normal distribution, or on some other appropriate statistical method.

In particular, normal ranges are established for each marker throughout gestation, using the Standard Risk subset (Appendix 1). For this purpose each value is treated as an independent observation. Results are then expressed as Standard Deviations Scores (Z-scores), showing how many standard deviations each result is from the expected value at that gestation. Adjustments are made for non-normality, and changes in both mean and standard deviation through gestation.

In one aspect of the predictive methods described herein, the Z-scores, derived from the markers as described in appendix 2, can be combined using the algorithms described in appendix 3 (all derived from logistic regression).

The level of sensitivity and specificity can be altered by altering the level at which a subject is considered to be at risk of PE. In some situations, e.g., when screening large numbers of women at low risk of PE, it is important to have high specificity. In other situations, it can be important to have a balance between high sensitivity and specificity, e.g., when considering individual women at high risk of PE a balance between high sensitivity and specificity is needed. Table 2 shows the performance of numerous combinations of markers based on fixing the specificity at 95% (False positive rate=5%), 90% (False positive rate=10%) and 85% (False positive rate=15%).

The technology described herein offers many benefits. In addition to facilitating accurate targeting of interventions, e.g., vitamin supplements, considerable saving on health care resources can be expected due to stratification of antenatal care and reduced neonatal special care costs. In the research and development area, identification of high risk patients will greatly facilitate future clinical trials. At present due to inadequate methods of prediction, large numbers of pregnant women unnecessarily receive interventions in clinical trials.

The method described above can be performed in conjunction with other tests for diagnostic indicators, such as levels of uric acid, etc.

The method can also be used in order to monitor the efficiency of a prophylactic treatment for preventing the development of PE, wherein a reduction in the risk of developing PE will be indicative of the prophylactic treatment working.

More than twenty biochemical markers have been shown previously to be associated with established PE and there would be no logical prior reason for choosing the specific combination of markers and measurements disclosed herein in any prospective longitudinal study for assessment of use as predictive indicators.

In a further aspect, there is provided a commercial package, such as a research or diagnostic kit for performing a method described herein. Such a kit can include reagents useful for determining the level of the markers selecting for detecting or predicting PE. Suitable agents for assaying for the markers include antibodies and other target binding molecules, enzyme linked immunoassay reagents, RIA reagents and reagents for Western blotting. The kit can also include apparatus for measuring the uterine artery waveform, for example, a Doppler Ultrasound apparatus. The kit can also include apparatus for measuring the blood pressure of the subject. The kit can also include a computer programmed with an algorithm for calculating the subject's risk of developing PE, instructions and other items useful for performing a method described herein.

The methods and commercial packages described herein can be useful for detecting or predicting pregnancy-associated disorders or syndromes with similar aetiology and/or symptoms as preeclampsia. Such preeclampsia related disorders or syndromes include, for example, pregnancy induced hypertension, HELLP syndrome, intrauterine growth retardation and superimposed gestosis.

Particular aspects of this technology are described by way of example, below.

EXAMPLES

Blood samples were obtained from and arterial Doppler was performed on 198 pregnant women who were recruited with risk factors for PE (chronic hypertension, diabetes, previous PE, chronic renal disease, antiphospholipid syndrome, Body Mass Index>30 in first pregnancies, abnormal uterine artery Doppler waveform). 172 were available for analysis; the remainder were not included due to miscarriage (n=5), stillbirth (n=3), termination of pregnancy (n=2) and lost to follow up (n=6), or withdrawal from the study (n=10). 19 women developed PE. The remaining 153 women form the high risk control group (HR). In addition, 95 nulliparous women without any of the previous risk factors were recruited as 'standard risk' controls (SR). 70 of these women had normal pregnancy outcome at term, from which the standard risk controls were selected.

Blood samples were taken at 11-14 weeks gestation, and then at 15-17, 19-21 and 23-35 weeks. After delivery the 19 cases of pre-eclampsia were matched 1:2 to high risk controls, and 1:2 with standard risk controls for biochemical markers. Blood markers and the results of Doppler ultrasound (diastolic notch; resistance index (RI); pulsatility index (PI)), alone and in combination were considered at 12, 16, 20 and 24 weeks. The biomarkers measured were: free PLGF, bound PLGF, total PLGF, soluble Flt-1, Leptin, PAI-1, PAI-2, MMP-9, ICAM and soluble TNF-alpha R1 (sTNFαR1). All of these other than sTNFαR1 were measured using Auto Delfia assays developed for this purpose. sTNFαR1 was measured using a commercially available ELISA assay (R&D Systems). Resistance index and presence of diastolic notch were derived from the uterine artery Doppler waveform.

Gestational-adjusted likelihood-ratio scores were created by establishing reference ranges in both cases and controls for the 13 indicators in both cases and controls (free PLGF, bound PLGF, total PLGF, MMP-9, Leptin, PAI-1, PAI-2, sFlt-1, sTNFαR1, ICAM, pulsatility index (PI), diastolic notch and resistance index (RI)). Bound PLGF was found to add nothing to the predictive power of free and total PLGF and was removed from further consideration. Soluble Flt was also excluded, as there were technical problems with the assay. For comparison, the combinations of markers considered in International Patent Application WO 02/37120 are also shown.

Normal ranges were established for each marker throughout gestation, using the Standard Risk subset (Appendix 1). For this purpose each value was treated as an independent observation. All results were then expressed as Standard Deviations Scores (Z-scores), showing how many standard deviations each result is from the expected value at that gestation. Adjustments were made for non-normality, and changes in both mean and standard deviation through gestation, according to the methods described below and in detail in appendix 2.

These gestation-adjusted Z-scores are summarised in Appendix 2 below, together with visit-by-visit comparisons. Means and SD were estimated by Tobit regression, with censoring at −2 and +2 (robust to outliers), following the method described in Amemiya T (1973) Regression analysis when the dependent variable is truncated Normal. Econometrica 41: 997-1016, as implemented for panel data in the statistical computing package Stata, release 9 (StataCorp, College Station, Tex.). Significance tests are carried out both by a random effects Tobit regression (censored at −2 and +2) and by Generalised Estimating Equations following the method described in Liang K-Y and Zeiger SL (1986). Longitudinal analysis using generalised linear models. Biometrika 73: 13-22, with robust Standard Errors, as described in Binder DA (1983). "On the variances of asymptotically normal estimators from complex surveys," *International Statistical Review* 51: 279-292, and implemented for panel data in the statistical computing package Stata, release 9 (StataCorp, College Station, Tex.).

The tests differ in the way they allow for extreme values and for repeated measures. Results by the two methods are similar, but not identical.

The performance of the individual indicators is given below in Table 1.

Receiver Operating Characteristic (ROC) areas are shown together with Sensitivity, and positive predictive values PPV for critical values chosen to give 5%, 10%, 15% false positive rates (FPR), equivalent to 95%, 90% and 85% specificity. All these terms are familiar to those well versed in medical statistics, and are explained in standard textbooks on the subject, for example Douglas Altman "Practical Statistics in Medical Research" Chapman & Hall, London (1991) pp 409-419. PPV is the probability of a woman becoming a case, given a positive test result. It can be calculated as (Prevalence*Sensitivity)/(Prevalence*sensitivity+(1−prevalence)*(1−Specificity)). For the purposes of these calculations, 5% Prevalence is assumed in low risk women, 15% in high risk women.

Based on these results, MMP-9, PLGF and soluble sTNFαR1 are selected for further work, optionally with one or more of diastolic notch, blood pressure (SBP or MAP), PAI-1, PAI-2, leptin and ICAM. The predicted performance of these indicators is given in Table 2, using simple logistic regression, without quadratic terms. Again, logistic regression is a standard method well known to those experienced in medical statistics, explained in Altman (1991), pages 351-364, and implemented in statistical packages such as Stata Version 9 (StataCorp, College Station, Tex.)

For a 5% false positive rate (95% specificity), the detection rate in high risk women using the biochemical markers alone is 56%, giving a positive predictive value of 66%. Including the systolic blood pressure raises the DR to 84% to and the PPV to 75%. In standard risk women, the same combination gives 80% DR and 46% PPV.

In conclusion, the methods described herein are capable of identifying at least 4 in 5 women likely to go on to develop pre-eclampsia if correctly used at a cost only 1 false alarm in 20 women tested. By itself this could reduce the number of antenatal visits needed by most women, and focus attention on those women most at risk.

All documents cited herein are incorporated by reference.

TABLE 1

Performance of individual indicators & established combinations
Individual markers are standardised as described elsewhere. Standard combinations are as in International Patent Application WO 02/37120.
Low values of free PLGF, total PLGF, PAI2, MMP-9, $\log_e$ (Free PLGF) − 3 * (PAI1:PAI2), PAI2 * Free PLGF are regarded as predictive of pre-eclampsia.
The previously published combinations: Leptin/Free PLGF, $\log_e$ (Free PLGF) − 3 * (PAI1:PAI2), PAI 1:PAI 2 ratio, PAI2 * Free PLGF (International Patent Application WO 02/37120) are included for comparison, as are the markers soluble FLT, MMP-2, Inhibin, VEGF and Adiponectin. Low values of soluble FLT, MMP-2, VEGF and Adiponectin are analysed as though predictive of PE.

| Predictor | Standardised Value | | 5% FPR | | 10% FPR | | 15% FPR | |
|---|---|---|---|---|---|---|---|---|
| | ROC Area | [95% CI] | DR | PPV | DR | PPV | DR | PPV |
| (1) PE vs Standard Risk | | | | | | | | |
| Visit 1: 11–14 weeks gestation | | | | | | | | |
| Free PLGF | 0.50 | (0.28 to 0.73) | 0.09 | 0.24 | 0.16 | 0.22 | 0.22 | 0.20 |
| sTNFαR1 | 0.80 | (0.64 to 0.97) | 0.35 | 0.55 | 0.48 | 0.46 | 0.58 | 0.40 |
| PAI2 | 0.49 | (0.24 to 0.74) | 0.15 | 0.34 | 0.21 | 0.27 | 0.26 | 0.23 |
| MMP-9 | 0.65 | (0.44 to 0.86) | 0.13 | 0.12 | 0.22 | 0.10 | 0.30 | 0.10 |
| Total PLGF | 0.51 | (0.29 to 0.73) | 0.04 | 0.04 | 0.09 | 0.04 | 0.14 | 0.05 |
| ICAM | 0.61 | (0.37 to 0.85) | 0.13 | 0.12 | 0.21 | 0.10 | 0.28 | 0.09 |
| PI | 0.76 | (0.49 to 1.00) | 0.37 | 0.57 | 0.46 | 0.45 | 0.53 | 0.38 |
| Resistance index | 0.64 | (0.29 to 1.00) | 0.22 | 0.44 | 0.30 | 0.35 | 0.37 | 0.30 |
| SBP | 0.84 | (0.67 to 1.00) | 0.61 | 0.68 | 0.68 | 0.55 | 0.73 | 0.46 |
| Notch | 0.76 | (0.67 to 0.85) | — | | — | | — | |
| Leptin/Free PLGF | 0.59 | (0.36 to 0.83) | 0.16 | 0.14 | 0.24 | 0.11 | 0.31 | 0.10 |

TABLE 1-continued

Performance of individual indicators & established combinations
Individual markers are standardised as described elsewhere. Standard combinations are as in
International Patent Application WO 02/37120.
Low values of free PLGF, total PLGF, PAI2, MMP-9, $\log_e$ (Free PLGF) − 3 * (PAI1:PAI2), PAI2 * Free
PLGF are regarded as predictive of pre-eclampsia.
The previously published combinations: Leptin/Free PLGF, $\log_e$ (Free PLGF) − 3 * (PAI1:PAI2),
PAI 1:PAI 2 ratio, PAI2 * Free PLGF (International Patent Application WO 02/37120) are included for
comparison, as are the markers soluble FLT, MMP-2, Inhibin, VEGF and Adiponectin. Low values of
soluble FLT, MMP-2, VEGF and Adiponectin are analysed as though predictive of PE.

| Predictor | Standardised Value | | 5% FPR | | 10% FPR | | 15% FPR | |
|---|---|---|---|---|---|---|---|---|
| | ROC Area | [95% CI] | DR | PPV | DR | PPV | DR | PPV |
| $\log_e$ (Free PLGF) − 3 * (PAI1:PAI2) | 0.56 | (0.32 to 0.80) | 0.07 | 0.06 | 0.13 | 0.06 | 0.19 | 0.06 |
| PAI 1:PAI 2 ratio | 0.45 | (0.22 to 0.68) | 0.22 | 0.19 | 0.29 | 0.13 | 0.33 | 0.10 |
| PAI2 * Free PLGF | 0.56 | (0.32 to 0.79) | 0.04 | 0.04 | 0.10 | 0.05 | 0.16 | 0.05 |
| Soluble FLT | 0.47 | (0.24 to 0.70) | 0.04 | 0.04 | 0.08 | 0.04 | 0.12 | 0.04 |
| MMP-2 | 0.62 | (0.40 to 0.85) | 0.20 | 0.17 | 0.28 | 0.13 | 0.34 | 0.11 |
| Inhibin | 0.46 | (0.22 to 0.71) | 0.13 | 0.12 | 0.18 | 0.09 | 0.23 | 0.07 |
| VEGF | 0.50 | (0.26 to 0.74) | 0.10 | 0.09 | 0.16 | 0.08 | 0.21 | 0.07 |
| Adiponectin | 0.56 | (0.31 to 0.82) | 0.25 | 0.21 | 0.31 | 0.14 | 0.35 | 0.11 |
| Visit 2: 15–17 weeks gestation | | | | | | | | |
| Free PLGF | 0.66 | (0.47 to 0.85) | 0.30 | 0.52 | 0.39 | 0.41 | 0.45 | 0.34 |
| sTNFαR1 | 0.71 | (0.51 to 0.91) | 0.23 | 0.45 | 0.34 | 0.38 | 0.43 | 0.34 |
| PAI 2 | 0.63 | (0.39 to 0.87) | 0.37 | 0.57 | 0.44 | 0.43 | 0.48 | 0.36 |
| MMP-9 | 0.48 | (0.28 to 0.69) | 0.03 | 0.03 | 0.07 | 0.04 | 0.11 | 0.04 |
| Total PLGF | 0.70 | (0.49 to 0.91) | 0.30 | 0.24 | 0.40 | 0.17 | 0.47 | 0.14 |
| ICAM | 0.64 | (0.43 to 0.85) | 0.13 | 0.12 | 0.22 | 0.10 | 0.30 | 0.09 |
| PI | 0.53 | (0.24 to 0.82) | 0.17 | 0.37 | 0.24 | 0.30 | 0.30 | 0.26 |
| Resistance index | 0.51 | (0.25 to 0.77) | 0.08 | 0.21 | 0.13 | 0.19 | 0.18 | 0.18 |
| SBP | 0.80 | (0.65 to 0.95) | 0.42 | 0.60 | 0.53 | 0.49 | 0.61 | 0.42 |
| Notch | 0.55 | (0.32 to 0.79) | — | — | — | — | — | — |
| Leptin/Free PLGF | 0.74 | (0.53 to 0.95) | 0.39 | 0.29 | 0.47 | 0.20 | 0.53 | 0.16 |
| $\log_e$ (Free PLGF) − 3 * (PAI1:PAI2) | 0.70 | (0.47 to 0.92) | 0.48 | 0.34 | 0.54 | 0.22 | 0.58 | 0.17 |
| PAI 1:PAI 2 ratio | 0.56 | (0.33 to 0.79) | 0.25 | 0.21 | 0.32 | 0.14 | 0.37 | 0.11 |
| PAI2 * Free PLGF | 0.73 | (0.49 to 0.98) | 0.45 | 0.32 | 0.51 | 0.21 | 0.56 | 0.16 |
| Soluble FLT | 0.60 | (0.36 to 0.85) | 0.23 | 0.19 | 0.30 | 0.14 | 0.35 | 0.11 |
| MMP-2 | 0.48 | (0.24 to 0.72) | 0.13 | 0.12 | 0.19 | 0.09 | 0.24 | 0.08 |
| Inhibin | 0.46 | (0.23 to 0.68) | 0.14 | 0.13 | 0.20 | 0.10 | 0.25 | 0.08 |
| VEGF | 0.66 | (0.45 to 0.87) | 0.18 | 0.16 | 0.28 | 0.13 | 0.35 | 0.11 |
| Adiponectin | 0.58 | (0.32 to 0.85) | 0.26 | 0.21 | 0.32 | 0.14 | 0.37 | 0.11 |
| Visit 3: 19–21 weeks gestation | | | | | | | | |
| Free PLGF | 0.75 | (0.59 to 0.91) | 0.43 | 0.60 | 0.51 | 0.47 | 0.56 | 0.40 |
| sTNFαR1 | 0.71 | (0.52 to 0.90) | 0.24 | 0.46 | 0.33 | 0.37 | 0.40 | 0.32 |
| PAI2 | 0.63 | (0.42 to 0.83) | 0.31 | 0.52 | 0.38 | 0.40 | 0.43 | 0.34 |
| MMP-9 | 0.60 | (0.41 to 0.79) | 0.23 | 0.19 | 0.31 | 0.14 | 0.38 | 0.12 |
| Total PLGF | 0.71 | (0.56 to 0.87) | 0.20 | 0.18 | 0.32 | 0.15 | 0.42 | 0.13 |
| ICAM | 0.70 | (0.54 to 0.87) | 0.21 | 0.18 | 0.32 | 0.14 | 0.40 | 0.12 |
| PI | 0.65 | (0.43 to 0.86) | 0.04 | 0.13 | 0.10 | 0.15 | 0.17 | 0.17 |
| Resistance index | 0.72 | (0.57 to 0.87) | 0.13 | 0.32 | 0.24 | 0.30 | 0.34 | 0.29 |
| SBP | 0.79 | (0.66 to 0.92) | 0.36 | 0.56 | 0.49 | 0.46 | 0.58 | 0.40 |
| Notch | 0.72 | (0.58 to 0.86) | — | — | — | — | — | — |
| Leptin/Free PLGF | 0.75 | (0.59 to 0.91) | 0.39 | 0.29 | 0.48 | 0.20 | 0.55 | 0.16 |
| $\log_e$ (Free PLGF) − 3 * (PAI1:PAI2) | 0.85 | (0.73 to 0.96) | 0.55 | 0.37 | 0.64 | 0.25 | 0.70 | 0.20 |
| PAI 1:PAI 2 ratio | 0.71 | (0.55 to 0.87) | 0.54 | 0.36 | 0.56 | 0.23 | 0.58 | 0.17 |
| PAI2 * Free PLGF | 0.79 | (0.65 to 0.93) | 0.46 | 0.32 | 0.55 | 0.23 | 0.62 | 0.18 |
| Soluble FLT | 0.54 | (0.33 to 0.75) | 0.16 | 0.15 | 0.22 | 0.10 | 0.26 | 0.08 |
| MMP-2 | 0.58 | (0.38 to 0.77) | 0.21 | 0.18 | 0.28 | 0.13 | 0.34 | 0.11 |
| Inhibin | 0.53 | (0.33 to 0.74) | 0.17 | 0.15 | 0.23 | 0.11 | 0.28 | 0.09 |
| VEGF | 0.68 | (0.50 to 0.86) | 0.18 | 0.16 | 0.28 | 0.13 | 0.36 | 0.11 |
| Adiponectin | 0.62 | (0.42 to 0.83) | 0.23 | 0.20 | 0.30 | 0.14 | 0.36 | 0.11 |
| Visit 4: 23–25 weeks gestation | | | | | | | | |
| Free PLGF | 0.77 | (0.61 to 0.92) | 0.61 | 0.68 | 0.65 | 0.53 | 0.67 | 0.44 |
| sTNFαR1 | 0.73 | (0.57 to 0.89) | 0.16 | 0.36 | 0.29 | 0.34 | 0.39 | 0.32 |
| PAI 2 | 0.69 | (0.49 to 0.88) | 0.45 | 0.62 | 0.51 | 0.47 | 0.55 | 0.39 |
| MMP-9 | 0.61 | (0.43 to 0.79) | 0.20 | 0.18 | 0.29 | 0.13 | 0.36 | 0.11 |
| Total PLGF | 0.73 | (0.56 to 0.90) | 0.37 | 0.28 | 0.46 | 0.19 | 0.52 | 0.15 |
| ICAM | 0.80 | (0.65 to 0.96) | 0.36 | 0.28 | 0.49 | 0.21 | 0.58 | 0.17 |
| PI | 0.84 | (0.71 to 0.97) | 0.62 | 0.69 | 0.66 | 0.54 | 0.69 | 0.45 |
| Resistance Index | 0.76 | (0.60 to 0.91) | 0.41 | 0.59 | 0.50 | 0.47 | 0.57 | 0.40 |
| SBP | 0.82 | (0.68 to 0.96) | 0.55 | 0.66 | 0.64 | 0.53 | 0.69 | 0.45 |
| Notch | 0.79 | (0.65 to 0.93) | — | — | — | — | — | — |
| Leptin/Free PLGF | 0.80 | (0.65 to 0.96) | 0.61 | 0.39 | 0.65 | 0.25 | 0.68 | 0.19 |
| $\log_e$ (Free PLGF) − 3 * (PAI1:PAI2) | 0.85 | (0.73 to 0.98) | 0.67 | 0.41 | 0.70 | 0.27 | 0.73 | 0.20 |
| PAI 1:PAI 2 ratio | 0.81 | (0.65 to 0.96) | 0.61 | 0.39 | 0.65 | 0.26 | 0.69 | 0.19 |

TABLE 1-continued

Performance of individual indicators & established combinations
Individual markers are standardised as described elsewhere. Standard combinations are as in
International Patent Application WO 02/37120.
Low values of free PLGF, total PLGF, PAI2, MMP-9, $\log_e$ (Free PLGF) − 3 * (PAI1:PAI2), PAI2 * Free
PLGF are regarded as predictive of pre-eclampsia.
The previously published combinations: Leptin/Free PLGF, $\log_e$ (Free PLGF) − 3 * (PAI1:PAI2),
PAI 1:PAI 2 ratio, PAI2 * Free PLGF (International Patent Application WO 02/37120) are included for
comparison, as are the markers soluble FLT, MMP-2, Inhibin, VEGF and Adiponectin. Low values of
soluble FLT, MMP-2, VEGF and Adiponectin are analysed as though predictive of PE.

| Predictor | Standardised Value | | 5% FPR | | 10% FPR | | 15% FPR | |
|---|---|---|---|---|---|---|---|---|
| | ROC Area | [95% CI] | DR | PPV | DR | PPV | DR | PPV |
| PAI2 * Free PLGF | 0.79 | (0.62 to 0.95) | 0.62 | 0.39 | 0.66 | 0.26 | 0.69 | 0.19 |
| Soluble FLT | 0.49 | (0.26 to 0.71) | 0.14 | 0.13 | 0.18 | 0.09 | 0.21 | 0.07 |
| MMP-2 | 0.59 | (0.39 to 0.78) | 0.16 | 0.14 | 0.24 | 0.11 | 0.30 | 0.10 |
| Inhibin | 0.53 | (0.32 to 0.75) | 0.27 | 0.22 | 0.33 | 0.15 | 0.38 | 0.12 |
| VEGF | 0.66 | (0.48 to 0.84) | 0.24 | 0.20 | 0.32 | 0.15 | 0.39 | 0.12 |
| Adiponectin | 0.65 | (0.42 to 0.87) | 0.35 | 0.27 | 0.42 | 0.18 | 0.46 | 0.14 |
| All time periods | | | | | | | | |
| Free PLGF | 0.70 | (0.61 to 0.79) | 0.48 | 0.63 | 0.53 | 0.63 | 0.56 | 0.40 |
| sTNFαR1 | 0.74 | (0.65 to 0.83) | 0.25 | 0.47 | 0.37 | 0.47 | 0.45 | 0.35 |
| PAI2 | 0.62 | (0.51 to 0.73) | 0.35 | 0.55 | 0.41 | 0.55 | 0.46 | 0.35 |
| MMP-9 | 0.59 | (0.49 to 0.68) | 0.16 | 0.14 | 0.24 | 0.14 | 0.31 | 0.10 |
| ICAM | 0.69 | (0.60 to 0.79) | 0.21 | 0.18 | 0.32 | 0.18 | 0.40 | 0.12 |
| Total PLGF | 0.68 | (0.59 to 0.77) | 0.24 | 0.20 | 0.34 | 0.20 | 0.42 | 0.13 |
| PI | 0.69 | (0.58 to 0.81) | 0.40 | 0.59 | 0.47 | 0.59 | 0.52 | 0.38 |
| Resistance Index | 0.68 | (0.57 to 0.78) | 0.23 | 0.45 | 0.33 | 0.45 | 0.40 | 0.32 |
| SBP | 0.81 | (0.74 to 0.88) | 0.49 | 0.63 | 0.59 | 0.63 | 0.66 | 0.44 |
| Notch | 0.70 | (0.61 to 0.78) | — | — | — | — | — | — |
| Leptin/Free PLGF | 0.74 | (0.65 to 0.83) | 0.47 | 0.33 | 0.53 | 0.33 | 0.58 | 0.17 |
| $\log_e$ (Free PLGF) − 3 * (PAI1:PAI2) | 0.78 | (0.69 to 0.86) | 0.51 | 0.35 | 0.57 | 0.35 | 0.61 | 0.18 |
| PAI 1:PAI 2 ratio | 0.66 | (0.56 to 0.75) | 0.33 | 0.26 | 0.40 | 0.26 | 0.44 | 0.13 |
| PAI2 * Free PLGF | 0.74 | (0.65 to 0.83) | 0.48 | 0.34 | 0.54 | 0.34 | 0.58 | 0.17 |
| Soluble FLT | 0.52 | (0.41 to 0.63) | 0.15 | 0.14 | 0.21 | 0.14 | 0.25 | 0.08 |
| MMP-2 | 0.57 | (0.46 to 0.67) | 0.17 | 0.16 | 0.25 | 0.16 | 0.31 | 0.10 |
| Inhibin | 0.51 | (0.40 to 0.62) | 0.19 | 0.16 | 0.25 | 0.16 | 0.30 | 0.10 |
| VEGF | 0.64 | (0.54 to 0.73) | 0.18 | 0.16 | 0.26 | 0.16 | 0.33 | 0.10 |
| Adiponectin | 0.60 | (0.49 to 0.72) | 0.27 | 0.22 | 0.34 | 0.22 | 0.39 | 0.12 |
| (2) PE vs. High Risk | | | | | | | | |
| Visit 1: 11–14 weeks gestation | | | | | | | | |
| Free PLGF | 0.71 | (0.50 to 0.92) | 0.13 | 0.31 | 0.24 | 0.31 | 0.34 | 0.28 |
| sTNFαR1 | 0.81 | (0.65 to 0.97) | 0.05 | 0.15 | 0.23 | 0.15 | 0.45 | 0.34 |
| MMP-9 | 0.73 | (0.51 to 0.94) | 0.32 | 0.53 | 0.43 | 0.53 | 0.50 | 0.37 |
| VEGF | 0.55 | (0.30 to 0.79) | 0.08 | 0.21 | 0.15 | 0.21 | 0.21 | 0.20 |
| ICAM | 0.48 | (0.24 to 0.73) | 0.08 | 0.22 | 0.13 | 0.22 | 0.18 | 0.17 |
| SBP | 0.63 | (0.46 to 0.81) | 0.10 | 0.27 | 0.20 | 0.27 | 0.28 | 0.25 |
| Notch | 0.75 | (0.68 to 0.82) | — | — | — | — | — | — |
| Leptin/Free PLGF | 0.65 | (0.40 to 0.89) | 0.23 | 0.45 | 0.32 | 0.45 | 0.38 | 0.31 |
| $\log_e$ (Free PLGF) − 3 * (PAI1:PAI2) | 0.66 | (0.44 to 0.89) | 0.07 | 0.20 | 0.15 | 0.20 | 0.24 | 0.22 |
| PAI 1:PAI 2 ratio | 0.44 | (0.20 to 0.67) | 0.28 | 0.50 | 0.34 | 0.50 | 0.37 | 0.31 |
| PAI2 * Free PLGF | 0.64 | (0.40 to 0.88) | 0.02 | 0.08 | 0.09 | 0.08 | 0.18 | 0.18 |
| Soluble FLT | 0.41 | (0.17 to 0.64) | 0.02 | 0.06 | 0.05 | 0.06 | 0.08 | 0.08 |
| MMP-2 | 0.53 | (0.29 to 0.78) | 0.13 | 0.32 | 0.20 | 0.32 | 0.26 | 0.23 |
| Inhibin | 0.40 | (0.16 to 0.64) | 0.06 | 0.18 | 0.10 | 0.18 | 0.14 | 0.14 |
| Total PLGF | 0.56 | (0.34 to 0.78) | 0.01 | 0.05 | 0.05 | 0.05 | 0.11 | 0.12 |
| Adiponectin | 0.60 | (0.36 to 0.84) | 0.22 | 0.43 | 0.29 | 0.43 | 0.35 | 0.29 |
| Visit 2: 15–17 weeks gestation | | | | | | | | |
| Free PLGF | 0.63 | (0.43 to 0.83) | 0.14 | 0.34 | 0.24 | 0.34 | 0.32 | 0.27 |
| sTNFαR1 | 0.73 | (0.52 to 0.94) | 0.22 | 0.44 | 0.34 | 0.44 | 0.43 | 0.34 |
| MMP-9 | 0.67 | (0.46 to 0.88) | 0.11 | 0.28 | 0.20 | 0.28 | 0.29 | 0.25 |
| Total PLGF | 0.59 | (0.37 to 0.81) | 0.08 | 0.21 | 0.15 | 0.21 | 0.23 | 0.21 |
| ICAM | 0.47 | (0.23 to 0.72) | 0.11 | 0.28 | 0.17 | 0.28 | 0.22 | 0.20 |
| SBP | 0.65 | (0.50 to 0.81) | 0.04 | 0.13 | 0.11 | 0.13 | 0.19 | 0.18 |
| Notch | 0.62 | (0.39 to 0.84) | — | — | — | — | — | — |
| Leptin/Free PLGF | 0.64 | (0.43 to 0.86) | 0.19 | 0.41 | 0.28 | 0.41 | 0.35 | 0.29 |
| $\log_e$ (Free PLGF) − 3 * (PAI1:PAI2) | 0.69 | (0.47 to 0.91) | 0.43 | 0.60 | 0.49 | 0.60 | 0.54 | 0.39 |
| PAI 1:PAI 2 ratio | 0.47 | (0.24 to 0.70) | 0.36 | 0.56 | 0.41 | 0.56 | 0.44 | 0.34 |
| PAI2 * Free PLGF | 0.67 | (0.44 to 0.90) | 0.21 | 0.43 | 0.31 | 0.43 | 0.38 | 0.31 |
| Soluble FLT | 0.53 | (0.29 to 0.78) | 0.11 | 0.29 | 0.18 | 0.29 | 0.23 | 0.21 |
| MMP-2 | 0.47 | (0.24 to 0.70) | 0.04 | 0.12 | 0.08 | 0.12 | 0.12 | 0.13 |
| Inhibin | 0.28 | (0.06 to 0.51) | 0.06 | 0.17 | 0.09 | 0.17 | 0.12 | 0.12 |

TABLE 1-continued

Performance of individual indicators & established combinations
Individual markers are standardised as described elsewhere. Standard combinations are as in
International Patent Application WO 02/37120.
Low values of free PLGF, total PLGF, PAI2, MMP-9, $\log_e$ (Free PLGF) − 3 * (PAI1:PAI2), PAI2 * Free
PLGF are regarded as predictive of pre-eclampsia.
The previously published combinations: Leptin/Free PLGF, $\log_e$ (Free PLGF) − 3 * (PAI1:PAI2),
PAI 1:PAI 2 ratio, PAI2 * Free PLGF (International Patent Application WO 02/37120) are included for
comparison, as are the markers soluble FLT, MMP-2, Inhibin, VEGF and Adiponectin. Low values of
soluble FLT, MMP-2, VEGF and Adiponectin are analysed as though predictive of PE.

| Predictor | Standardised Value | | 5% FPR | | 10% FPR | | 15% FPR | |
|---|---|---|---|---|---|---|---|---|
| | ROC Area | [95% CI] | DR | PPV | DR | PPV | DR | PPV |
| VEGF | 0.59 | (0.38 to 0.81) | 0.16 | 0.37 | 0.24 | 0.37 | 0.31 | 0.27 |
| Adiponectin | 0.64 | (0.41 to 0.87) | 0.21 | 0.43 | 0.30 | 0.43 | 0.36 | 0.30 |
| Visit 3: 19–21 weeks gestation | | | | | | | | |
| Free PLGF | 0.72 | (0.56 to 0.88) | 0.26 | 0.48 | 0.37 | 0.48 | 0.44 | 0.34 |
| sTNFαR1 | 0.70 | (0.51 to 0.89) | 0.11 | 0.28 | 0.21 | 0.28 | 0.30 | 0.26 |
| MMP-9 | 0.63 | (0.44 to 0.83) | 0.28 | 0.49 | 0.36 | 0.49 | 0.42 | 0.33 |
| Total PLGF | 0.60 | (0.42 to 0.78) | 0.05 | 0.15 | 0.12 | 0.15 | 0.19 | 0.19 |
| ICAM | 0.56 | (0.37 to 0.76) | 0.10 | 0.27 | 0.17 | 0.27 | 0.23 | 0.22 |
| SBP | 0.63 | (0.49 to 0.77) | 0.08 | 0.21 | 0.16 | 0.21 | 0.24 | 0.22 |
| Notch | 0.69 | (0.55 to 0.83) | — | — | — | — | — | — |
| Leptin/Free PLGF | 0.68 | (0.51 to 0.85) | 0.23 | 0.44 | 0.32 | 0.44 | 0.39 | 0.32 |
| $\log_e$ (Free PLGF) − 3 * (PAI1:PAI2) | 0.70 | (0.54 to 0.86) | 0.01 | 0.05 | 0.06 | 0.05 | 0.13 | 0.13 |
| PAI 1:PAI 2 ratio | 0.59 | (0.42 to 0.76) | 0.37 | 0.56 | 0.42 | 0.56 | 0.45 | 0.35 |
| PAI2 * Free PLGF | 0.67 | (0.51 to 0.84) | 0.16 | 0.36 | 0.27 | 0.36 | 0.37 | 0.30 |
| Soluble FLT | 0.38 | (0.20 to 0.56) | 0.09 | 0.24 | 0.12 | 0.24 | 0.15 | 0.15 |
| MMP-2 | 0.54 | (0.35 to 0.73) | 0.01 | 0.04 | 0.04 | 0.04 | 0.07 | 0.08 |
| Inhibin | 0.47 | (0.27 to 0.68) | 0.07 | 0.19 | 0.11 | 0.19 | 0.16 | 0.16 |
| VEGF | 0.60 | (0.40 to 0.79) | 0.18 | 0.39 | 0.25 | 0.39 | 0.30 | 0.26 |
| Adiponectin | 0.58 | (0.38 to 0.78) | 0.13 | 0.31 | 0.20 | 0.31 | 0.26 | 0.24 |
| Visit 4: 23–25 weeks gestation | | | | | | | | |
| Free PLGF | 0.68 | (0.51 to 0.85) | 0.52 | 0.65 | 0.57 | 0.65 | 0.60 | 0.42 |
| sTNFαR1 | 0.84 | (0.70 to 0.97) | 0.12 | 0.29 | 0.29 | 0.29 | 0.46 | 0.35 |
| MMP-9 | 0.60 | (0.40 to 0.79) | 0.25 | 0.47 | 0.33 | 0.47 | 0.39 | 0.32 |
| Total PLGF | 0.61 | (0.43 to 0.79) | 0.14 | 0.34 | 0.23 | 0.34 | 0.31 | 0.27 |
| ICAM | 0.71 | (0.54 to 0.89) | 0.18 | 0.38 | 0.29 | 0.38 | 0.38 | 0.31 |
| SBP | 0.68 | (0.52 to 0.84) | 0.23 | 0.45 | 0.33 | 0.45 | 0.41 | 0.32 |
| Notch | 0.75 | (0.61 to 0.88) | — | — | — | — | — | — |
| Leptin/Free PLGF | 0.77 | (0.61 to 0.93) | 0.55 | 0.66 | 0.60 | 0.66 | 0.63 | 0.43 |
| $\log_e$ (Free PLGF) − 3 * (PAI1:PAI2) | 0.74 | (0.59 to 0.90) | 0.52 | 0.65 | 0.58 | 0.65 | 0.62 | 0.42 |
| PAI 1:PAI 2 ratio | 0.68 | (0.50 to 0.86) | 0.34 | 0.54 | 0.42 | 0.54 | 0.47 | 0.36 |
| PAI2 * Free PLGF | 0.70 | (0.53 to 0.88) | 0.47 | 0.62 | 0.54 | 0.62 | 0.58 | 0.41 |
| Soluble FLT | 0.39 | (0.19 to 0.59) | 0.07 | 0.19 | 0.10 | 0.19 | 0.13 | 0.13 |
| MMP-2 | 0.56 | (0.37 to 0.75) | 0.03 | 0.09 | 0.07 | 0.09 | 0.13 | 0.13 |
| Inhibin | 0.48 | (0.26 to 0.69) | 0.21 | 0.42 | 0.27 | 0.42 | 0.31 | 0.27 |
| VEGF | 0.57 | (0.39 to 0.75) | 0.11 | 0.29 | 0.18 | 0.29 | 0.24 | 0.22 |
| Adiponectin | 0.62 | (0.42 to 0.82) | 0.08 | 0.22 | 0.15 | 0.22 | 0.22 | 0.21 |
| All | | | | | | | | |
| Free PLGF | 0.67 | (0.58 to 0.76) | 0.38 | 0.57 | 0.45 | 0.57 | 0.50 | 0.37 |
| sTNFαR1 | 0.78 | (0.70 to 0.86) | 0.08 | 0.23 | 0.22 | 0.23 | 0.35 | 0.29 |
| MMP-9 | 0.65 | (0.55 to 0.75) | 0.24 | 0.46 | 0.33 | 0.46 | 0.40 | 0.32 |
| Total PLGF | 0.59 | (0.49 to 0.68) | 0.07 | 0.21 | 0.15 | 0.21 | 0.23 | 0.21 |
| ICAM | 0.57 | (0.46 to 0.67) | 0.12 | 0.30 | 0.20 | 0.30 | 0.26 | 0.23 |
| SBP | 0.65 | (0.58 to 0.73) | 0.10 | 0.26 | 0.19 | 0.26 | 0.28 | 0.25 |
| Notch | 0.70 | (0.62 to 0.78) | — | — | — | — | — | — |
| Leptin/Free PLGF | 0.69 | (0.60 to 0.78) | 0.38 | 0.57 | 0.45 | 0.57 | 0.50 | 0.37 |
| $\log_e$ (Free PLGF) − 3 * (PAI1:PAI2) | 0.70 | (0.61 to 0.78) | 0.30 | 0.52 | 0.39 | 0.52 | 0.46 | 0.35 |
| PAI 1:PAI 2 ratio | 0.55 | (0.45 to 0.65) | 0.34 | 0.55 | 0.40 | 0.55 | 0.44 | 0.34 |
| PAI2 * Free PLGF | 0.67 | (0.57 to 0.76) | 0.31 | 0.52 | 0.40 | 0.52 | 0.46 | 0.35 |
| Soluble FLT | 0.42 | (0.32 to 0.53) | 0.07 | 0.21 | 0.12 | 0.21 | 0.15 | 0.15 |
| MMP-2 | 0.53 | (0.43 to 0.63) | 0.03 | 0.10 | 0.07 | 0.10 | 0.12 | 0.13 |
| Inhibin | 0.42 | (0.32 to 0.53) | 0.10 | 0.26 | 0.15 | 0.26 | 0.19 | 0.18 |
| VEGF | 0.57 | (0.47 to 0.67) | 0.12 | 0.30 | 0.19 | 0.30 | 0.25 | 0.23 |
| Adiponectin | 0.60 | (0.50 to 0.71) | 0.13 | 0.31 | 0.21 | 0.31 | 0.27 | 0.24 |

TABLE 2

Combinations of predictors (performance estimated by simple logistic regression). Details of calculation of prediction scores and critical values are given in Appendix 3. Subjects with prediction scores above the critical values are treated as test positive.

| Predictor | Standardised Value | | 5% FPR | | 10% FPR | | 15% FPR | |
|---|---|---|---|---|---|---|---|---|
| | ROC Area | [95% CI] | DR | PPV | DR | PPV | DR | PPV |
| PE vs Standard risk <br> All visits, prevalence .05 | | | | | | | | |
| Z(sTNFαR1), Z(MMP-9) | 0.78 | (0.70 to 0.87) | 0.43 | 0.31 | 0.52 | 0.22 | 0.54 | 0.16 |
| Z(sTNFαR1), Z(MMP-9) diastolic notch | 0.89 | (0.81 to 0.96) | 0.46 | 0.33 | 0.64 | 0.25 | 0.75 | 0.21 |
| Z(sTNFαR1), Z(free PLGF) | 0.79 | (0.71 to 0.87) | 0.33 | 0.26 | 0.49 | 0.20 | 0.53 | 0.16 |
| Z(sTNFαR1), Z(free PLGF) diastolic notch | 0.84 | (0.76 to 0.93) | 0.35 | 0.27 | 0.62 | 0.24 | 0.69 | 0.20 |
| Z(sTNFαR1), Z(MMP-9), Z(free PLGF) | 0.83 | (0.75 to 0.91) | 0.43 | 0.31 | 0.57 | 0.23 | 0.57 | 0.17 |
| Z(sTNFαR1), Z(MMP-9), Z(PAI-2) | 0.83 | (0.75 to 0.91) | 0.39 | 0.29 | 0.56 | 0.23 | 0.59 | 0.17 |
| Z(sTNFαR1), Z(MMP-9), Z(SBP) | 0.91 | (0.85 to 0.96) | 0.65 | 0.41 | 0.80 | 0.30 | 0.83 | 0.22 |
| Z(Free PlGF), Z(MMP-9), Z(sTNFaR1), Z(PAI-2), Z(SBP) diastolic notch | 0.98 | (0.96 to 1.00) | 0.77 | 0.45 | 1.00 | 0.34 | 1.00 | 0.26 |
| Z(sTNFαR1), Z(MMP-9), Z(MAP) | 0.92 | (0.87 to 0.97) | 0.76 | 0.44 | 0.80 | 0.30 | 0.80 | 0.22 |
| Z(sTNFαR1), Z(MMP-9), Z(leptin) | 0.78 | (0.70 to 0.87) | 0.40 | 0.30 | 0.51 | 0.21 | 0.56 | 0.16 |
| Z(sTNFαR1), Z(MMP-9), Z(total PLGF) | 0.83 | (0.76 to 0.90) | 0.36 | 0.28 | 0.45 | 0.19 | 0.57 | 0.17 |
| Z(sTNFαR1), Z(MMP-9), Z(PAI-1) | 0.77 | (0.68 to 0.87) | 0.46 | 0.33 | 0.49 | 0.20 | 0.54 | 0.16 |
| Z(sTNFαR1), Z(MMP-9), Z(sICAM) | 0.83 | (0.75 to 0.90) | 0.39 | 0.29 | 0.52 | 0.22 | 0.72 | 0.20 |
| *Previous combinations (International Patent application WO 02/37120)* | | | | | | | | |
| Z(PAI2/PAI1) | 0.66 | (0.56 to 0.75) | 0.30 | 0.24 | 0.36 | 0.16 | 0.36 | 0.11 |
| Z(Leptin/free PLGF) | 0.74 | (0.65 to 0.83) | 0.38 | 0.29 | 0.42 | 0.18 | 0.56 | 0.16 |
| Z(PAI2 * free PLGF) | 0.74 | (0.65 to 0.83) | 0.33 | 0.26 | 0.40 | 0.17 | 0.46 | 0.14 |
| Z(log_e(Free PlGF) − 3 * (PAI1/PAI2)) | 0.78 | (0.69 to 0.86) | 0.35 | 0.27 | 0.42 | 0.18 | 0.54 | 0.16 |
| *Comparison combination* | | | | | | | | |
| Z(sFlt-1), Z(MMP-2), Z(Inhibin), Z(VEGF), Z(total PLGF), Z(adiponectin) | 0.66 | (0.55 to 0.78) | 0.45 | 0.32 | 0.50 | 0.21 | 0.55 | 0.16 |
| PE vs HIGH risk <br> All visits, prevalence .15 | | | | | | | | |
| Z(sTNFαR1), Z(MMP-9) | 0.82 | (0.74 to 0.90) | 0.33 | 0.54 | 0.48 | 0.46 | 0.63 | 0.43 |
| Z(sTNFαR1), Z(MMP-9) diastolic notch | 0.89 | (0.82 to 0.97) | 0.61 | 0.68 | 0.64 | 0.53 | 0.71 | 0.46 |
| Z(sTNFαR1), Z(free PLGF) | 0.83 | (0.75 to 0.91) | 0.33 | 0.53 | 0.51 | 0.47 | 0.53 | 0.39 |
| Z(sTNFαR1), Z(free PLGF) diastolic notch | 0.89 | (0.82 to 0.97) | 0.62 | 0.68 | 0.62 | 0.52 | 0.69 | 0.45 |
| Z(sTNFαR1), Z(MMP-9), Z(free PLGF) | 0.85 | (0.77 to 0.92) | 0.40 | 0.59 | 0.55 | 0.49 | 0.69 | 0.45 |
| Z(sTNFαR1), Z(MMP-9), Z(PAI-2) | 0.84 | (0.76 to 0.92) | 0.32 | 0.53 | 0.51 | 0.47 | 0.66 | 0.44 |
| Z(sTNFαR1), Z(MMP-9), Z(SBP) | 0.85 | (0.78 to 0.92) | 0.48 | 0.63 | 0.61 | 0.52 | 0.61 | 0.42 |
| Z(Free PlGF), Z(MMP-9), Z(sTNFaR1), Z(PAI-2), Z(SBP) diastolic notch | 0.95 | (0.88 to 1.00) | 0.86 | 0.75 | 0.91 | 0.62 | 0.91 | 0.52 |
| Z(sTNFαR1), Z(MMP-9), Z(MAP) | 0.85 | (0.78 to 0.92) | 0.50 | 0.64 | 0.57 | 0.50 | 0.67 | 0.44 |
| Z(sTNFαR1), Z(MMP-9), Z(leptin) | 0.81 | (0.73 to 0.89) | 0.33 | 0.54 | 0.49 | 0.46 | 0.51 | 0.38 |
| Z(sTNFαR1), Z(MMP-9), Z(total PLGF) | 0.83 | (0.75 to 0.91) | 0.30 | 0.51 | 0.34 | 0.38 | 0.64 | 0.43 |
| Z(sTNFαR1), Z(MMP-9), Z(PAI-1) | 0.79 | (0.70 to 0.88) | 0.32 | 0.53 | 0.44 | 0.44 | 0.49 | 0.36 |
| Z(sTNFαR1), Z(MMP-9), Z(sICAM) | 0.82 | (0.74 to 0.90) | 0.30 | 0.52 | 0.52 | 0.48 | 0.65 | 0.43 |
| *Previous recommendations (International Patent application WO 02/37120)* | | | | | | | | |
| Z(PAI2/PAI1) | 0.55 | (0.45 to 0.65) | 0.10 | 0.26 | 0.12 | 0.17 | 0.20 | 0.19 |
| Z(Leptin/free PLGF) | 0.69 | (0.60 to 0.78) | 0.21 | 0.43 | 0.31 | 0.35 | 0.40 | 0.32 |
| Z(PAI2 * free PLGF) | 0.67 | (0.57 to 0.76) | 0.23 | 0.45 | 0.31 | 0.36 | 0.33 | 0.28 |
| Z(log_e(Free PlGF) − 3 * (PAI1/PAI2)) | 0.70 | (0.61 to 0.78) | 0.19 | 0.40 | 0.27 | 0.32 | 0.35 | 0.29 |

APPENDIX 1

Normal Ranges for Selected Predictors of PE—Established in Standard Risk Women with Normal Outcomes The transformations have three components:

In most cases log and power transformations are used to achieve approximate Gaussian (Normal) distributions The mean values at each gestation is estimated by a quadratic curve (not shown); the coefficient of variation (and hence the standard deviation) by a linear function For all subjects, a Z-score (standard deviations score) is estimated; showing the number of standard deviations the value is above or below the expected value at that gestation.

Plots are established (not shown) that show the standard risk women with reference lines at 3%, 50%, 97%, representing −2, 0, 2 SD above or below the mean.

The transformations given remove the effect of gestation in standard risk women on both the mean and spread of the values. These are used to standardise the values in high risk controls and PE cases.

The ratios PAI2/PAI1 and Leptin (pg/mL)/Free PLGF (pg/mL) are used, to keep ratios>1. 3 subjects with PAI2<2*PAI1 excluded from estimates of PAI1, PAI2, and all combinations involving these.

To understand how the formulae are to be used, consider a woman with a Free PLGF of 194.11 and DBP of 66 at 19 weeks and 6 days gestation. Considering DBP first; there are no transformations to worry about, so the process is relatively straightforward.

The expected $DBP = 75.1 -$
$1.09 * \text{gestational age (weeks)} + .02695 * \text{gestational age (weeks)}^2 =$
$75.1 - 1.09 * (19 + 6/7) + .02695 * (19 + 6/7)^2 = 64.1$ The SD of $DBP =$
$(0.113 + 0.00076 * \text{gestational age (weeks)}) * \text{expected value} =$
$(0.113 + 0.00076 * (19 + 6/7)) * 64.1 = 8.21$ The Z-score is (actual value − expected value)/Standard deviation =
$(66 − 64.1)/8.21 = 0.23$ In considering Free PLGF, there are two transformations to consider. The expected value is first worked out for $\log_{10}$(Free PLGF). Both actual and expected values are then raised to the power 0.669. Standard Deviations and Z-scores are worked out for these new values.

The actual value of $\log_{10}$(Free PLGF) is $\log_{10}(194.11) = 2.288$

The expected value of $\log_{10}$(Free $PLGF$) =
$-.9681 + .261 * \text{gestational age (weeks)} -$
$.00445 * \text{gestational age (weeks)}^2 =$
$-.9681 + .261 * (19 + 6/7) - .00445 * (19 + 6/7)^2 = 2.46$ Raising these to power 0.669 gives 1.740 and 1.826

The standard deviation of $\log_{10}(\text{Free } PLGF)^{0.669} =$
$(-0.0050 * \text{gestational age (weeks)} + 0.184) * .669 * (\text{expected } value^{.669}) =$
$(-0.0050 * (19 + 6/7) + 0.184) * .669 * (2.46^{.669}) = 0.103$ The Z-score is again (actual value − expected value)/Standard
deviation = $(1.74 − 1.826)/0.103 = −0.84$ Free PLGF Model: $\log_{10}$(Free PLGF)=−0.968+0.261*gestational age (weeks)−0.00445*gestational age(weeks)$^2$ SD($\log_{10}$(Free PLGF)$^{0.669}$)=(−0.0050*gestational age (weeks)+0.184)*0.669*(expected value$^{0.669}$)

Total PLGF

Model: $\log_{10}$(Total PLGF)=0.446+0.1638*gestational age (weeks)−0.00241*gestational age(weeks)$^2$ SD($\log_{10}$(Total PLGF)$^{2.52}$)=(−0.0028*gestational age (weeks)+0.120)*2.52*(expected value$^{2.52}$)

PAI-1

Model: $\log_{10}$(PAI-1)=−0.519+0.1388*gestational age (weeks)−0.00257*gestational age(weeks)$^2$ SD($\log_{10}$(PAI-1)$^{0.502}$)=(0.278−0.008*gestational age (weeks))*expected value*0.502

SD($\log_{10}$(PAI-1)$^{0.502}$)=(−0.0077*gestational age(weeks)+0.278)*0.502*(expected value$^{0.502}$)

PAI-2

Model: $\log_{10}$(PAI-2)=0.19+0.1177*gestational age(weeks)−0.00162*gestational age(weeks)$^2$ SD($\log_{10}$(PAI-2)$^{0.935}$)=(−0.0045*gestational age(weeks)+0.156)*0.935*(expected value$^{0.935}$)

Leptin

Model: $\log_{10}$(Leptin)=1.44−0.0061*gestational age (weeks)+0.00045*gestational age(weeks)$^2$ SD($\log_{10}$(leptin)$^{1.93}$)=(−0.0015*gestational age(weeks)+0.194)*1.93*(expected value$^{1.93}$)

STNFαR1

Model: $\log_{10}$(STNFαR1)=2.87−0.0026*gestational age (weeks)+0.00022*gestational age(weeks)$^2$ SD($\log_{10}$(STNFαR1)$^{-10.3}$)=(0.0007*gestational age (weeks)+0.012)*−10.3*(expected value$^{-10.3}$)

MMP-9

Model: $\log_{10}$(MMP-9)=3.11−0.0612*gestational age (weeks)+0.0018*gestational age(weeks)$^2$ SD($\log_{10}$(MMP-9)$^{1.62}$)=(−0.0024*gestational age(weeks)+0.157)*1.62*(expected value$^{1.62}$)

Pulsatility Index

Model: PI=2.04+0.0901*gestational age(weeks)−0.00475*gestational age(weeks)$^2$

SD(PI)=(0.524−0.009*gestational age(weeks))*expected value

Resistance Index

Model: RI=0.797−0.0108*gestational age(weeks)−8.6e−05*gestational age(weeks)$^2$ SD(RI)=(0.302−0.006*gestational age(weeks))*expected value

SBP

Model: SBP=112+0.0131*gestational age(weeks)−0.00724*gestational age(weeks)$^2$

SD(SBP)=(0.040+0.002*gestational age(weeks))*expected value

DBP

Model: DBP=75.1+−1.09*gestational age(weeks)+0.02695*gestational age(weeks)$^2$

SD(DBP)=(0.113+0.00076*gestational age(weeks))*expected value

MAP (=DBP+(SBP−DBP)/3

Model: MAP=87.3−0.7161*gestational age(weeks)+0.01542*gestational age(weeks)$^2$ SD(MAP)=(0.062+0.002*gestational age(weeks))*expected value

PAI-2/PLGF

Model: $\log_{10}$(PAI-2/PLGF)=−0.555+0.3565*gestational age(weeks)−0.00552*gestational age(weeks)$^2$ SD($\log_{10}$(PAI-2/PLGF)$^{1.54}$)=(−0.0037*gestational age(weeks)+0.130)*1.54*(expected value$^{1.54}$)

PAI2/PAI1

Model: $\log_{10}$(PAI2/PAI1)=0.625−0.0143*gestational age(weeks)+0.00077*gestational age(weeks)$^2$ SD($\log_{10}$(PAI2/PAI1)$^{-0.049}$)=(−0.0025*gestational age(weeks)+0.267)*−0.049*(expected value$^{-0.049}$)

Leptin/Free PLGF

Model: $\log_{10}$(Leptin/Free PLGF)=5.8−0.3118*gestational age(weeks)+0.00611*gestational age(weeks)$^2$ SD($\log_{10}$(Leptin/Free PLGF)$^{2.09}$)=(0.0036*gestational age(weeks)+0.081)*2.09*(expected value$^{2.09}$)

$\log_e$ (Free PLGF)−3*(PAI1:PAI2)

Model: $\log_e$(Free PLGF−*PAI-1/PAI-2)=−2.2+0.5004*gestational age(weeks)−0.00706*gestational age(weeks)$^2$ SD($\log_e$(Free PLGF−*PAI-1/PAI-2))=(0.267−0.008*gestational age(weeks))*expected value

APPENDIX 2

Estimated Means and SD of the Z-Scores by Visit and Outcome Group

Means and SD are estimated by Generalised Estimating Equations (GEE) with robust Standard Errors. Graphs are shown with error bars based on SE. Significance tests are carried out based on both the GEE model and a random effects Tobit regression (censored at 2 and +2). The GEE approach gives equal weight to each woman (rather than each blood sample), and allows for repeated measurements, and corrects the Standard Errors.

| Z score for Free PLGF (pg/ml) | | | | | | Significance tests | |
|---|---|---|---|---|---|---|---|
| | SR mean | SD | HR mean | SD | PE mean | SD | PE vs SR | PE vs HR |
| 11–14 wks | −0.101 | 1.088 | 0.748 | 1.499 | −0.225 | 1.027 | 0.770 | 0.060 |
| 15–17 wks | 0.036 | 0.796 | 0.062 | 1.183 | −0.540 | 1.100 | 0.105 | 0.112 |
| 19–21 wks | −0.011 | 0.923 | −0.171 | 1.288 | −1.074 | 1.272 | 0.003 | 0.014 |
| 23–25 wks | 0.027 | 1.110 | −0.331 | 1.576 | −1.213 | 1.701 | 0.008 | 0.060 |
| All | (censored at +/−2 SD) | | | | | | 0.018 | 0.021 |
| All | (by GEE with robust SE) | | | | | | 0.004 | 0.005 |

| Z score for Total PLGF (pg/ml) | | | | | | Significance tests | |
|---|---|---|---|---|---|---|---|
| | SR mean | SD | HR mean | SD | PE mean | SD | PE vs SR | PE vs HR |
| 11–14 wks | −0.077 | 1.076 | 0.209 | 1.309 | −0.127 | 0.973 | 0.904 | 0.464 |
| 15–17 wks | −0.017 | 0.786 | −0.342 | 1.181 | −0.894 | 1.231 | 0.017 | 0.164 |
| 19–21 wks | −0.038 | 1.075 | −0.485 | 1.269 | −0.949 | 1.075 | 0.009 | 0.186 |
| 23–25 wks | 0.093 | 1.017 | −0.459 | 1.521 | −1.029 | 1.527 | 0.007 | 0.183 |
| All | (censored at +/−2 SD) | | | | | | 0.005 | 0.028 |
| All | (by GEE with robust SE) | | | | | | 0.003 | 0.057 |

| Z score for PAI 1 (ng/ml) | | | | | | Significance tests | |
|---|---|---|---|---|---|---|---|
| | SR mean | SD | HR mean | SD | PE mean | SD | PE vs SR | PE vs HR |
| 11–14 wks | 0.206 | 1.156 | 0.554 | 1.220 | 0.104 | 0.773 | 0.813 | 0.330 |
| 15–17 wks | 0.054 | 1.105 | −0.069 | 0.674 | 0.110 | 1.191 | 0.859 | 0.617 |
| 19–21 wks | −0.098 | 0.977 | 0.203 | 0.950 | 0.354 | 0.906 | 0.127 | 0.614 |
| 23–25 wks | 0.131 | 0.931 | 0.412 | 1.100 | 1.051 | 1.011 | 0.003 | 0.041 |
| All | (censored at +/−2 SD) | | | | | | 0.123 | 0.324 |
| All | (by GEE with robust SE) | | | | | | 0.145 | 0.489 |

Z score for PAI 2 (ng/ml)

|  | SR mean | SD | HR mean | SD | PE mean | SD | Significance tests PE vs SR | PE vs HR |
|---|---|---|---|---|---|---|---|---|
| 11–14 wks | −0.212 | 1.267 | −0.209 | 1.722 | −0.083 | 1.650 | 0.793 | 0.865 |
| 15–17 wks | 0.120 | 0.934 | −0.457 | 1.320 | −0.564 | 2.486 | 0.202 | 0.989 |
| 19–21 wks | −0.096 | 0.829 | −0.613 | 1.479 | −0.658 | 1.665 | 0.190 | 0.944 |
| 23–25 wks | −0.001 | 1.032 | −0.618 | 1.161 | −1.239 | 2.630 | 0.024 | 0.477 |
| All | (censored at +/−2 SD) | | | | | | 0.001 | 0.614 |
| All | (by GEE with robust SE) | | | | | | 0.020 | 0.237 |

Z score for Leptin (ng/ml)

|  | SR mean | SD | HR mean | SD | PE mean | SD | Significance tests PE vs SR | PE vs HR |
|---|---|---|---|---|---|---|---|---|
| 11–14 wks | 0.095 | 1.042 | 0.623 | 1.079 | 0.439 | 1.178 | 0.388 | 0.653 |
| 15–17 wks | −0.037 | 0.964 | 0.376 | 1.044 | 0.553 | 1.165 | 0.103 | 0.650 |
| 19–21 wks | −0.011 | 1.102 | 0.311 | 0.965 | 0.424 | 1.133 | 0.180 | 0.744 |
| 23–25 wks | −0.040 | 0.984 | −0.015 | 0.942 | 0.505 | 1.182 | 0.077 | 0.093 |
| All | (censored at +/−2 SD) | | | | | | 0.000 | 0.000 |
| All | (by GEE with robust SE) | | | | | | 0.075 | 0.387 |

Z score for sTNFα-R1

|  | SR mean | SD | HR mean | SD | PE mean | SD | Significance tests PE vs SR | PE vs HR |
|---|---|---|---|---|---|---|---|---|
| 11–14 wks | 0.023 | 1.147 | −1.131 | 2.884 | 1.547 | 1.293 | 0.013 | 0.001 |
| 15–17 wks | −0.007 | 0.933 | −0.114 | 1.016 | 0.877 | 1.156 | 0.022 | 0.012 |
| 19–21 wks | −0.119 | 0.965 | −0.179 | 1.276 | 0.582 | 1.210 | 0.053 | 0.047 |
| 23–25 wks | 0.119 | 1.058 | −0.490 | 1.123 | 0.941 | 0.878 | 0.014 | 0.000 |
| All | (censored at +/−2 SD) | | | | | | 0.011 | 0.000 |
| All | (by GEE with robust SE) | | | | | | 0.003 | 0.000 |

Z score for MMP 9

|  | SR mean | SD | HR mean | SD | PE mean | SD | Significance tests PE vs SR | PE vs HR |
|---|---|---|---|---|---|---|---|---|
| Visit 1 | −0.007 | 1.060 | 0.305 | 0.802 | −0.584 | 1.102 | 0.135 | 0.027 |
| Visit 2 | −0.007 | 0.939 | 0.540 | 0.955 | 0.028 | 0.855 | 0.748 | 0.135 |
| Visit 3 | 0.073 | 1.000 | 0.136 | 0.896 | −0.427 | 1.143 | 0.123 | 0.091 |
| Visit 4 | 0.026 | 1.066 | −0.055 | 0.845 | −0.511 | 1.158 | 0.102 | 0.167 |
| All | (Censored at +/−2 SD) | | | | | | 0.100 | 0.021 |
| All | (by GEE with robust SE) | | | | | | 0.094 | 0.021 |

Z score for Pulsatility Index

|  | SR mean | SD | HR mean | SD | PE mean | SD | Significance tests PE vs SR | PE vs HR |
|---|---|---|---|---|---|---|---|---|
| 11–14 wks | 0.141 | 1.013 | 0.466 | 1.102 | 1.389 | 1.500 | 0.026 | 0.100 |
| 15–17 wks | −0.172 | 0.825 | −0.097 | 0.806 | 0.102 | 1.205 | 0.531 | 0.662 |
| 19–21 wks | −0.026 | 0.983 | −0.070 | 0.931 | 0.410 | 0.875 | 0.264 | 0.199 |
| 23–25 wks | 0.006 | 0.909 | 0.449 | 1.000 | 1.421 | 1.130 | 0.001 | 0.016 |

-continued

Z score for Pulsatility Index

|  | SR mean | SD | HR mean | SD | PE mean | SD | Significance tests | |
|---|---|---|---|---|---|---|---|---|
|  |  |  |  |  |  |  | PE vs SR | PE vs HR |
| All | (censored at +/−2 SD) |  |  |  |  |  | 0.006 | 0.022 |
| All | (by GEE with robust SE) |  |  |  |  |  | 0.031 | 0.077 |

Z score for Resistance Index

|  | SR mean | SD | HR mean | SD | PE mean | SD | Significance tests | |
|---|---|---|---|---|---|---|---|---|
|  |  |  |  |  |  |  | PE vs SR | PE vs HR |
| 11–14 wks | 0.044 | 1.002 | 0.228 | 0.855 | 0.744 | 1.418 | 0.169 | 0.321 |
| 15–17 wks | 0.030 | 0.901 | 0.025 | 0.816 | 0.045 | 0.948 | 0.969 | 0.958 |
| 19–21 wks | −0.127 | 0.952 | 0.098 | 1.003 | 0.647 | 0.908 | 0.014 | 0.069 |
| 23–25 wks | 0.068 | 0.907 | 0.532 | 1.113 | 1.088 | 1.005 | 0.006 | 0.101 |
| All | (censored at +/−2 SD) |  |  |  |  |  | 0.001 | 0.034 |
| All | (by GEE with robust SE) |  |  |  |  |  | 0.006 | 0.063 |

Z score for SBP

|  | SR mean | SD | HR mean | SD | PE mean | SD | Significance tests | |
|---|---|---|---|---|---|---|---|---|
|  |  |  |  |  |  |  | PE vs SR | PE vs HR |
| 11–14 wks | 0.025 | 0.930 | 1.103 | 2.029 | 1.922 | 1.530 | 0.001 | 0.070 |
| 15–17 wks | −0.045 | 0.956 | 0.612 | 1.845 | 1.711 | 1.676 | 0.001 | 0.024 |
| 19–21 wks | −0.053 | 1.236 | 0.776 | 1.531 | 1.609 | 1.498 | 0.000 | 0.047 |
| 23–25 wks | 0.026 | 0.859 | 0.817 | 1.138 | 1.651 | 1.413 | 0.000 | 0.016 |
| All | (censored at +/−2 SD) |  |  |  |  |  | 0.000 | 0.002 |
| All | (by GEE with robust SE) |  |  |  |  |  | 0.000 | 0.004 |

Z score for DBP

|  | SR mean | SD | HR mean | SD | PE mean | SD | Significance tests | |
|---|---|---|---|---|---|---|---|---|
|  |  |  |  |  |  |  | PE vs SR | PE vs HR |
| 11–14 wks | −0.004 | 0.982 | 0.827 | 1.389 | 0.851 | 1.485 | 0.052 | 0.994 |
| 15–17 wks | −0.100 | 0.989 | 0.586 | 1.398 | 0.736 | 1.319 | 0.033 | 0.677 |
| 19–21 wks | 0.140 | 1.034 | 0.538 | 1.074 | 1.144 | 0.858 | 0.001 | 0.028 |
| 23–25 wks | −0.048 | 0.986 | 0.453 | 1.180 | 1.696 | 1.265 | 0.000 | 0.000 |
| All | (censored at +/−2 SD) |  |  |  |  |  | 0.000 | 0.007 |
| All | (by GEE with robust SE) |  |  |  |  |  | 0.000 | 0.012 |

Z score for Mean Arterial Pressure

|  | SR mean | SD | HR mean | SD | PE mean | SD | Significance tests | |
|---|---|---|---|---|---|---|---|---|
|  |  |  |  |  |  |  | PE vs SR | PE vs HR |
| 11–14 wks | 0.010 | 0.959 | 1.017 | 1.646 | 1.313 | 1.169 | 0.003 | 0.336 |
| 15–17 wks | −0.086 | 0.980 | 0.682 | 1.481 | 1.316 | 1.539 | 0.002 | 0.155 |
| 19–21 wks | 0.098 | 1.154 | 0.721 | 1.292 | 1.400 | 1.011 | 0.000 | 0.031 |
| 23–25 wks | −0.017 | 0.952 | 0.633 | 1.093 | 1.771 | 1.251 | 0.000 | 0.000 |
| All | (censored at +/−2 SD) |  |  |  |  |  | 0.000 | 0.008 |
| All | (by GEE with robust SE) |  |  |  |  |  | 0.000 | 0.004 |

Z score for PAI2 * Total PLGF

|  | SR mean | SD | HR mean | SD | PE mean | SD | Significance tests | |
|---|---|---|---|---|---|---|---|---|
|  |  |  |  |  |  |  | PE vs SR | PE vs HR |
| 11–14 wks | −0.158 | 1.206 | 0.004 | 1.697 | −0.296 | 1.118 | 0.793 | 0.577 |
| 15–17 wks | −0.002 | 0.832 | −0.471 | 1.280 | −1.535 | 2.223 | 0.009 | 0.128 |
| 19–21 wks | −0.062 | 0.973 | −0.595 | 1.439 | −1.140 | 1.368 | 0.007 | 0.178 |
| 23–25 wks | 0.108 | 1.053 | −0.629 | 1.441 | −1.428 | 2.088 | 0.002 | 0.182 |
| All | (censored at +/−2 SD) |  |  |  |  |  | 0.000 | 0.000 |
| All | (by GEE with robust SE) |  |  |  |  |  | 0.002 | 0.056 |

Z score for PAI1/PAI2

|  | SR mean | SD | HR mean | SD | PE mean | SD | Significance tests | |
|---|---|---|---|---|---|---|---|---|
|  |  |  |  |  |  |  | PE vs SR | PE vs HR |
| 11–14 wks | 0.277 | 1.006 | 0.640 | 1.574 | 0.176 | 1.616 | 0.773 | 0.414 |
| 15–17 wks | −0.057 | 1.254 | 0.382 | 1.458 | 0.333 | 1.812 | 0.488 | 0.886 |
| 19–21 wks | 0.010 | 1.075 | 0.609 | 1.423 | 0.932 | 1.165 | 0.016 | 0.359 |
| 23–25 wks | 0.051 | 0.946 | 0.753 | 1.123 | 1.608 | 1.439 | 0.000 | 0.038 |
| All | (censored at +/−2 SD) |  |  |  |  |  | 0.001 | 0.295 |
| All | (by GEE with robust SE) |  |  |  |  |  | 0.069 | 0.209 |

Z score for leptin/PLGF

|  | SR mean | SD | HR mean | SD | PE mean | SD | Significance tests | |
|---|---|---|---|---|---|---|---|---|
|  |  |  |  |  |  |  | PE vs SR | PE vs HR |
| 11–14 wks | 0.091 | 1.149 | 0.410 | 1.297 | 0.464 | 1.409 | 0.440 | 0.946 |
| 15–17 wks | −0.002 | 0.838 | 0.435 | 0.927 | 0.839 | 1.109 | 0.011 | 0.256 |
| 19–21 wks | 0.002 | 1.002 | 0.464 | 1.052 | 0.769 | 1.111 | 0.014 | 0.318 |
| 23–25 wks | −0.101 | 1.065 | 0.135 | 1.209 | 0.849 | 1.289 | 0.009 | 0.051 |
| All | (censored at +/−2 SD) |  |  |  |  |  | 0.000 | 0.001 |
| All | (by GEE with robust SE) |  |  |  |  |  | 0.006 | 0.104 |

Z score for $\log_e$(Total PLGF) − 3 * (PAI1:PAI2)

|  | SR mean | SD | HR mean | SD | PE mean | SD | Significance tests | |
|---|---|---|---|---|---|---|---|---|
|  |  |  |  |  |  |  | PE vs SR | PE vs HR |
| 11–14 wks | −0.298 | 1.263 | −0.258 | 2.140 | −0.565 | 1.192 | 0.628 | 0.519 |
| 15–17 wks | −0.104 | 0.957 | −0.529 | 1.339 | −1.855 | 2.485 | 0.016 | 0.131 |
| 19–21 wks | 0.001 | 1.094 | −0.739 | 1.512 | −1.481 | 1.223 | 0.000 | 0.057 |
| 23–25 wks | 0.043 | 1.054 | −0.679 | 1.498 | −1.844 | 1.656 | 0.000 | 0.017 |
| All | (censored at +/−2 SD) |  |  |  |  |  | 0.000 | 0.021 |
| All | (by GEE with robust SE) |  |  |  |  |  | 0.000 | 0.031 |

APPENDIX 3

Combination of Z-Scores into Composite Prediction Scores, and Assessment Against Critical Values For each composite score, the chosen Z-scores (calculated as described in appendix 1) are each multiplied by a fixed parameter, and summed, with a further constant added. The higher the prediction score the greater the risk of PE. Women who do not develop PE will generally have negative scores.

Parameters are given separately for prediction of PE vs high risk and of PE vs standard risk controls. The resulting values are compared with the critical values listed later. Parameters are presented in matrix form. Variable names are abbreviated as below:

z_freeplgf: Z(Free PLGF)

z_mmp9: Z(MMP-9)

z_stnfr1: Z(sTNFαR1)

z_pai2: Z(PAI-2)

z_sbp: Z(SBP)

notch: add only if arterial notch is present on Doppler ultrasound scan z_map: Z(MAP)

z_leptin: Z(Leptin)

z_totalplgf_sr: Z(Total PLGF)

z_pai1: Z(PAI-1)

z_sicam: Z(icam)

To demonstrate the principle, consider a woman of standard risk (i.e., with no particular risk factors for PE) who has sTNFαR1 and MMP-9 measured at a routine visit. On calculations, it is found that sTNFαR1 is slightly high (Z-score=1.2) MMP-9 very slightly low (Z score=−0.7). Neither value alone would cause concern. For administrative reasons, the clinic does not want to deal with more than 5% false positives, so has set the required FPR at 5%, and critical value at 0.12 (page 33, line 12).

Using the first matrix, her predictions score is 1.0432029*1.2−0.34696031*0.7−1.2863186=−0.28. This is less than the critical value, so the test is regarded as negative. The test would also be negative if the FPR was 10%; but if the clinic had set the FPR at 15% making the critical value −0.32, it would have been treated as positive.

If a Doppler ultrasound scan were performed and found no notch, the second matrix would be used. The prediction score would be 0.61090612*1.2−0.59709505*0.7−2.1966031=−1.9, an unambiguous negative result. If there was a notch, 2.7545618 would be added to the score, giving 0.87. This value needs to be compared to the second line of the table of critical values (page 33, line 14). Now, the result is negative for an FPR of 5% but positive for an FPR of 10% or 15%.

| | | For prediction of PE vs standard risk | | | | |
|---|---|---|---|---|---|---|
| b[1, 3] | z_stnfr1_sr | z_mmp9_sr | _cons | | | |
| y1 | 1.0432029 | −.34696031 | −1.2863186 | | | |
| b[1, 4] | z_stnfr1_sr | z_mmp9_sr | notch | _cons | | |
| y1 | .61090612 | −.59709505 | 2.7545618 | −2.1966031 | | |
| b[1, 3] | z_stnfr1_sr | z_freeplgf_sr | _cons | | | |
| y1 | .81384545 | −.53030671 | −1.5053348 | | | |
| b[1, 4] | z_stnfr1_sr | z_freeplgf_sr | notch | _cons | | |
| y1 | .26926822 | −.55020866 | 1.8888846 | −2.1814126 | | |
| b[1, 4] | z_stnfr1_sr | z_mmp9_sr | z_freeplgf_sr | _cons | | |
| y1 | 1.0738543 | −.19184711 | −.57021054 | −1.5267719 | | |
| b[1, 4] | z_stnfr1_sr | z_mmp9_sr | z_pai2_sr | _cons | | |
| y1 | 1.1534334 | −.3877764 | −.52279565 | −1.5507775 | | |
| b[1, 4] | z_stnfr1_sr | z_mmp9_sr | z_sbp_sr | _cons | | |
| y1 | 1.0301201 | −.38423421 | 1.4740355 | −2.1781847 | | |
| b[1, 7] | z_freeplgf_sr | z_mmp9_sr | z_stnfr1_sr | z_pai2_sr | z_sbp_sr | notch |
| y1 | −2.0250666 | −.65920058 | .59080375 | .19069115 | 3.6054897 | 1.9389349 |
| | _cons | | | | | |
| y1 | −5.7557371 | | | | | |
| b[1, 4] | z_stnfr1_sr | z_mmp9_sr | z_map_sr | _cons | | |
| y1 | 1.3379544 | −.10787412 | 1.6728738 | −2.3193343 | | |
| b[1, 4] | z_stnfr1_sr | z_mmp9_sr | z_leptin_sr | _cons | | |
| y1 | .98383643 | −.36584237 | .39760579 | −1.2927683 | | |
| b[1, 4] | z_stnfr1_sr | z_mmp9_sr | z_totalplgf_sr | _cons | | |
| y1 | 1.1851669 | −.1844576 | −.65271362 | −1.5679957 | | |
| b[1, 4] | z_stnfr1_sr | z_mmp9_sr | z_pai1_sr | _cons | | |
| y1 | .94282693 | −.30127994 | .12890895 | −1.2214146 | | |
| b[1, 4] | z_stnfr1_sr | z_mmp9_sr | z_sicam_sr | _cons | | |
| y1 | .99344876 | −.33604467 | .6909771 | −1.5493951 | | |
| b[1, 2] | z_pai2pai1_sr | _cons | | | | |
| y1 | −.15004057 | −1.0637463 | | | | |
| b[1, 2] | z_leptin_plgf_sr | _cons | | | | |
| y1 | .77674067 | −1.3431946 | | | | |
| b[1, 2] | z_pai2_plgf_sr | _cons | | | | |
| y1 | −.75667183 | −1.3920582 | | | | |
| logit pe | | | | | | |
| z_plgf_pai_e_sr | | | | | | |
| if pe\|sr, nolog | | | | | | |
| b[1, 2] | z_plgf_pai_e_sr | _cons | | | | |
| y1 | −.70432698 | −1.4878685 | | | | |
| b[1, 7] | z_flt1_sr | z_mmp2_sr | z_inhibin_sr | z_vegf_sr | z_totalplgf_sr | |
| y1 | .35582686 | −.16394511 | −.07078584 | −.27345864 | −.34067951 | |
| | z_adiponectin_sr | _cons | | | | |
| y1 | −.20935986 | −.9211228 | | | | |

| | Critical values | | |
|---|---|---|---|
| | 5% FPR | 10% FPR | 15% FPR |
| z_stnfr1_sr z_mmp9_sr | 0.12 | −0.19 | −0.32 |
| z_stnfr1_sr z_mmp9_sr notch | 1.02 | −0.03 | −0.68 |
| z_stnfr1_sr z_freeplgf_sr | 0.32 | −0.01 | −0.35 |
| z_stnfr1_sr z_freeplgf_sr notch | 0.66 | −0.22 | −0.92 |
| z_stnfr1_sr z_mmp9_sr z_freeplgf_sr | 0.52 | −0.10 | −0.29 |
| z_stnfr1_sr z_mmp9_sr z_pai2_sr | 0.67 | −0.16 | −0.28 |

-continued

| | | | | |
|---|---|---|---|---|
| z_stnfr1_sr z_mmp9_sr z_sbp_sr | 0.47 | −0.55 | −0.96 | |
| z_freeplgf_sr z_mmp9_sr z_stnfr1_sr z_pai2_sr z_sbp_sr notch | 0.22 | −1.28 | −2.06 | |
| z_stnfr1_sr z_mmp9_sr z_map_sr | 0.25 | −0.46 | −0.85 | |
| z_stnfr1_sr z_mmp9_sr z_leptin_sr | 0.48 | −0.09 | −0.34 | |
| z_stnfr1_sr z_mmp9_sr z_totalplgf_sr | 0.65 | 0.29 | −0.06 | |
| z_stnfr1_sr z_mmp9_sr z_pai1_sr | 0.13 | −0.12 | −0.22 | |
| z_stnfr1_sr z_mmp9_sr z_sicam_sr | 0.51 | 0.12 | −0.38 | |
| Previous combinations (International Patent application WO 02/37120) | | | | |
| z_pai2pai1_sr | −0.78 | −0.84 | −0.86 | |
| z_leptin_plgf_sr | −0.18 | −0.28 | −0.59 | |
| z_pai2_plgf_sr | −0.18 | −0.46 | −0.59 | |
| z_plgf_pai_e_sr | 0.04 | −0.42 | −0.77 | |
| Comparison combination | | | | |
| z_flt1_sr z_mmp2_sr z_inhibin_sr z_vegf_sr z_totalplgf_sr z_adiponectin_sr | −0.17 | −0.28 | −0.36 | |

For prediction of PE vs high risk

| | | | | | |
|---|---|---|---|---|---|
| b[1, 3] | z_stnfr1_sr | z_mmp9_sr | _cons | | |
| y1 | .88498059 | −.72536714 | −.94524474 | | |
| b[1, 4] | z_stnfr1_sr | z_mmp9_sr | notch | _cons | |
| y1 | .87523318 | −1.1270949 | 2.8218524 | −2.2408897 | |
| b[1, 3] | z_stnfr1_sr | z_freeplgf_sr | _cons | | |
| y1 | .86134793 | −.57855919 | −.87119207 | | |
| b[1, 4] | z_stnfr1_sr | z_freeplgf_sr | notch | _cons | |
| y1 | .80939968 | −.52511392 | 2.1766235 | −1.8037314 | |
| b[1, 4] | z_stnfr1_sr | z_mmp9_sr | z_freeplgf_sr | _cons | |
| y1 | .84869018 | −.47779192 | −.5639567 | −.87878531 | |
| b[1, 4] | z_stnfr1_sr | z_mmp9_sr | z_pai2_sr | _cons | |
| y1 | .85771221 | −.6995626 | −.46065059 | −1.025472 | |
| b[1, 4] | z_stnfr1_sr | z_mmp9_sr | z_sbp_sr | _cons | |
| y1 | .85569662 | −.7670603 | .51384748 | −1.5029548 | |
| b[1, 7] | z_freeplgf_sr | z_mmp9_sr | z_stnfr1_sr | z_pai2_sr | z_sbp_sr | notch |
| y1 | −.4940046 | −1.5801611 | .78963882 | −.41251359 | .8577906 | 3.950109 |
| | _cons | | | | |
| y1 | −3.8968735 | | | | |
| b[1, 4] | z_stnfr1_sr | z_mmp9_sr | z_map_sr | _cons | |
| y1 | .88661071 | −.74080545 | .58578771 | −1.5753431 | |
| b[1, 4] | z_stnfr1_sr | z_mmp9_sr | z_leptin_sr | _cons | |
| y1 | .79373952 | −.49158458 | .34714359 | −.68989926 | |
| b[1, 4] | z_stnfr1_sr | z_mmp9_sr | z_totalplgf_sr | _cons | |
| y1 | .8689593 | −.52976047 | −.47183616 | −.90188186 | |
| b[1, 4] | z_stnfr1_sr | z_mmp9_sr | z_pai1_sr | _cons | |
| y1 | .75591297 | −.48766196 | −.00740248 | −.66806738 | |
| b[1, 4] | z_stnfr1_sr | z_mmp9_sr | z_sicam_sr | _cons | |
| y1 | .8626898 | −.71502332 | .21285119 | −1.0772888 | |
| b[1, 2] | z_pai2pai1_sr | _cons | | | |
| y1 | −.11241369 | −.87572122 | | | |
| logit pe z_leptin_plgf_sr if pe|hr, nolog | | | | | |
| b[1, 2] | z_leptin_plgf_sr | _cons | | | |
| y1 | .50677483 | −1.084977 | | | |
| logit pe z_pai2_plgf_sr if pe|hr, nolog | | | | | |
| b[1, 2] | z_pai2_plgf_sr | _cons | | | |
| y1 | −.43092466 | −1.0958821 | | | |
| b[1, 2] | z_plgf_pai_e_sr | _cons | | | |
| y1 | −.34371951 | −1.1250665 | | | |
| b[1, 7] | z_flt1_sr | z_mmp2_sr | z_inhibin_sr | z_vegf_sr | z_totalplgf_sr |
| y1 | .789795 | .23762254 | −.7119987 | −.33843105 | −.23128792 |
| | z_adiponectin_sr | _cons | | | |
| y1 | −.54010533 | −.06317101 | | | |

Critical values

| | 5% FPR | 10% FPR | 15% FPR |
|---|---|---|---|
| z_stnfr1_sr z_mmp9_sr | 0.74 | 0.20 | −0.15 |
| z_stnfr1_sr z_mmp9_sr notch | 0.21 | −0.14 | −0.50 |
| z_stnfr1_sr z_freeplgf_sr | 1.04 | 0.61 | 0.29 |
| z_stnfr1_sr z_freeplgf_sr notch | 0.75 | 0.51 | 0.07 |
| z_stnfr1_sr z_mmp9_sr z_freeplgf_sr | 1.13 | 0.33 | −0.05 |
| z_stnfr1_sr z_mmp9_sr z_pai2_sr | 1.12 | 0.63 | −0.03 |
| z_stnfr1_sr z_mmp9_sr z_sbp_sr | 0.63 | 0.08 | −0.20 |
| z_freeplgf_sr z_mmp9_sr z_stnfr1_sr z_pai2_sr z_sbp_sr notch | 0.58 | −0.92 | −1.31 |

| | | | |
|---|---|---|---|
| -continued | | | |
| z_stnfr1_sr z_mmp9_sr z_map_sr | 0.80 | 0.08 | −0.28 |
| z_stnfr1_sr z_mmp9_sr z_leptin_sr | 0.91 | 0.60 | 0.49 |
| z_stnfr1_sr z_mmp9_sr z_totalplgf_sr | 1.26 | 0.99 | 0.09 |
| z_stnfr1_sr z_mmp9_sr z_pai1_sr | 1.01 | 0.44 | 0.16 |
| z_stnfr1_sr z_mmp9_sr z_sicam_sr | 0.74 | 0.22 | −0.15 |
| Previous combinations (International Patent application WO 02/37120) | | | |
| z_pai2pai1_sr | −0.19 | −0.48 | −0.62 |
| z_leptin_plgf_sr | 0.07 | −0.16 | −0.35 |
| z_pai2_plgf_sr | −0.13 | −0.24 | −0.33 |
| z_plgf_pai_e_sr | 0.03 | −0.24 | −0.41 |

The invention claimed is:

1. A method of predicting pre-eclampsia (PE) comprising determining in a maternal sample obtained from a human subject levels of soluble tissue necrosis factor alpha receptor 1 (sTNFαR1) and placenta growth factor (PLGF), wherein a positive prediction is given when high sTNFαR1 level and low PLGF level compared to normal levels in pregnant humans are determined.

2. The method according to claim 1, further comprising: determining the presence or absence of a diastolic notch in a uterine artery waveform obtained from the human subject, wherein a positive prediction is given when high sTNFαR1 and low PLGF compared to normal levels in pregnant humans, and presence of a notch are determined.

3. The method according to claim 1, further comprising determining in a maternal sample obtained from the human subject the level of Matrix Metalloproteinase-9 (MMP-9), wherein a positive prediction is given when high sTNFαR1, low MMP-9, and low PLGF compared to normal levels in pregnant humans are determined.

4. The method according to claim 1 additionally comprising the step of measuring one or more haemodynamic variables in the human subject.

5. A method of predicting pre-eclampsia (PB) comprising:
determining in a maternal sample obtained from a human subject levels of soluble tissue necrosis factor alpha receptor 1 (sTNFαR1) and placenta growth factor (PLGF); and
predicting pre-eclampsia for the human subject when high sTNFαR1 level and low PLGF level are found compared to normal levels in pregnant humans.

6. The method of claim 1 or 5 further comprising the step of prescribing vitamin supplements for the human subject based on the prediction.

7. The method of claim 1 or 5 further comprising the step of prescribing aspirin for the human subject based on the prediction.

8. The method of claim 1 or 5 further comprising the step of prescribing a prophylactic therapy for the human subject based on the prediction.

9. The method of claim 1 or 5 further comprising the step of assigning the human subject to a group for a clinical trial based on the prediction.

10. The method of claim 1 or 5 further comprising the step of monitoring the efficiency of a prophylactic treatment in the human subject based on the prediction.